(12) United States Patent
Bise et al.

(10) Patent No.: US 9,378,545 B2
(45) Date of Patent: Jun. 28, 2016

(54) CULTURE MEDIUM INFORMATION REGISTRATION SYSTEM, COLONY DETECTION DEVICE, PROGRAM AND SANITARY MANAGEMENT SYSTEM

(71) Applicant: DAI NIPPON PRINTING CO., LTD., Tokyo-to (JP)

(72) Inventors: Ryoma Bise, Tokyo-to (JP); Yuji Tsuzuki, Tokyo-to (JP); Masanori Kagota, Tokyo-to (JP); Rui Saitou, Tokyo-to (JP); Hitoshi Kyoutani, Tokyo-to (JP)

(73) Assignee: DAI NIPPON PRINTING CO., LTD., Tokyo-to (JP)

( * ) Notice: Subject to any disclaimer, the term of this patent is extended or adjusted under 35 U.S.C. 154(b) by 0 days.

(21) Appl. No.: 14/422,293

(22) PCT Filed: Aug. 21, 2013

(86) PCT No.: PCT/JP2013/072311
§ 371 (c)(1),
(2) Date: Feb. 18, 2015

(87) PCT Pub. No.: WO2014/030674
PCT Pub. Date: Feb. 27, 2014

(65) Prior Publication Data
US 2015/0243014 A1 Aug. 27, 2015

(30) Foreign Application Priority Data
Aug. 23, 2012 (JP) .................................. 2012-184666

(51) Int. Cl.
*G06K 9/00* (2006.01)
*G06T 7/00* (2006.01)
(Continued)

(52) U.S. Cl.
CPC .............. *G06T 7/0004* (2013.01); *C12M 41/36* (2013.01); *C12M 41/48* (2013.01); *C12Q 1/06* (2013.01);
(Continued)

(58) Field of Classification Search
CPC ... G01N 35/00871; C12M 41/48; C12M 41/36; G06F 17/3028; G06T 7/004; G06T 7/0004; G06T 5/001; G06T 7/408; G06T 2207/10024; G06T 2207/30128; G06T 2207/30242; G06K 9/6267; G06K 9/52; G06K 9/4652; G06K 9/00147; G06K 9/6247; C12Q 1/06
USPC .......................................................... 382/110
See application file for complete search history.

(56) References Cited

U.S. PATENT DOCUMENTS

2009/0087075 A1    4/2009  Kii et al.

FOREIGN PATENT DOCUMENTS

| CN | 102565395 A | * | 7/2012 | ........... G01N 33/569 |
| JP | 2003-116593 A | | 4/2003 | |

(Continued)

OTHER PUBLICATIONS

Thorsten Dörge, et al; "Direct identification of pure Penicillium species using image analysis", Journal of microbiological Methods, vol. 41, pp. 121-133; Jul. 2000.

(Continued)

*Primary Examiner* — Gregory F Cunningham
(74) *Attorney, Agent, or Firm* — Ladas & Parry LLP

(57) ABSTRACT

The sanitary management system S includes a plurality of portable communication terminal devices 10, a manager terminal device 20 and a server device 40. The server device 40: (1) extracts two or more feature values related to the color of each pixel constituting a culture medium image; (2) executes statistical analysis based on distribution of pixels of the culture medium image by using a coordinate system prescribed by the extracted two or more feature values of each pixel, and calculates a linear function prescribing relation of the two or more feature values in each pixel; and (3) detects the colonies in the culture medium image based on the calculated linear function and counts the number of colonies.

13 Claims, 22 Drawing Sheets

(51) Int. Cl.
*C12Q 1/06* (2006.01)
*G01N 35/00* (2006.01)
*C12M 1/34* (2006.01)
*G06F 17/30* (2006.01)
*G06K 9/46* (2006.01)
*G06K 9/52* (2006.01)
*G06K 9/62* (2006.01)
*G06T 5/00* (2006.01)
*G06T 7/40* (2006.01)
*C12M 1/36* (2006.01)

(52) U.S. Cl.
CPC ...... *G01N 35/00871* (2013.01); *G06F 17/3028* (2013.01); *G06K 9/0014* (2013.01); *G06K 9/00147* (2013.01); *G06K 9/4652* (2013.01); *G06K 9/52* (2013.01); *G06K 9/6247* (2013.01); *G06K 9/6267* (2013.01); *G06T 5/001* (2013.01); *G06T 7/004* (2013.01); *G06T 7/408* (2013.01); *G01N 2035/00881* (2013.01); *G06T 2207/10024* (2013.01); *G06T 2207/30128* (2013.01); *G06T 2207/30242* (2013.01)

(56) References Cited

FOREIGN PATENT DOCUMENTS

| | | | |
|---|---|---|---|
| JP | 2007-306889 A | 11/2007 | |
| JP | 2011-212013 A | 10/2011 | |
| JP | 2011-229413 A | 11/2011 | |
| JP | 2011229413 A * | 11/2011 | ............... C12M 1/34 |
| WO | 2007/136074 A1 | 11/2007 | |
| WO | 2011/115218 A1 | 9/2011 | |
| WO | WO 2011115218 A1 * | 9/2011 | ......... G01N 33/6848 |

OTHER PUBLICATIONS

Michael Putman, et al; "Simplified method to automatically count bacterial colony forming unit", Journal of Immunological Methods, vol. 302, pp. 99-102; Available online Jun. 20, 2005.
International Search Report dated Sep. 25, 2013; PCT/JP2013/072311.

* cited by examiner

FIG. 3

WORK INSTRUCTION SHEET

DOP FOOD CO. LTD.
DATE: 2012/5/9

INSTRUCTION SHEET ID (WORK ID) 71a

| PRODUCT | GRAPE JELLY |
|---|---|
| CODE | BDZ-180 |
| LOT No. | 20120510-A |
| QUANTITY | 50,000 |

| DATE | 2012/05/10 | | |
|---|---|---|---|
| START TIME | 08:30 | END TIME | 16:30 |

| LINE | LINE A |
|---|---|

| PROCESS | |
|---|---|
| THROW MATERIAL (PROCESS 1) | |
| MIX (PROCESS 2) | |
| FILL UP (PROCESS 3) | |
| BOIL (PROCESS 4) | |
| WRAPPING (PROCESS 5) | |
| PACKING (PROCESS 6) | |

PROCESS ID (WORK ID) 71b

WORK INSTRUCTION SHEET 70

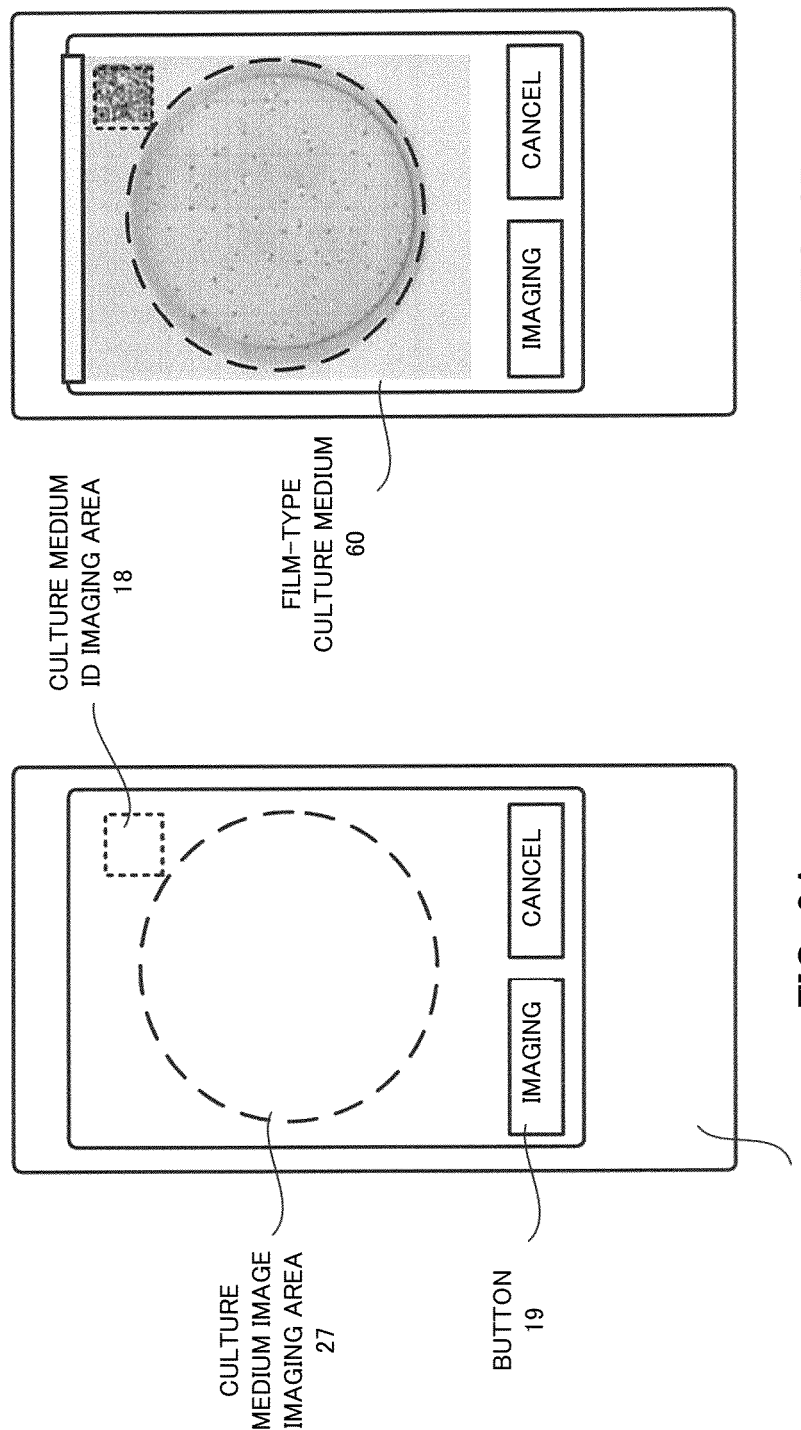

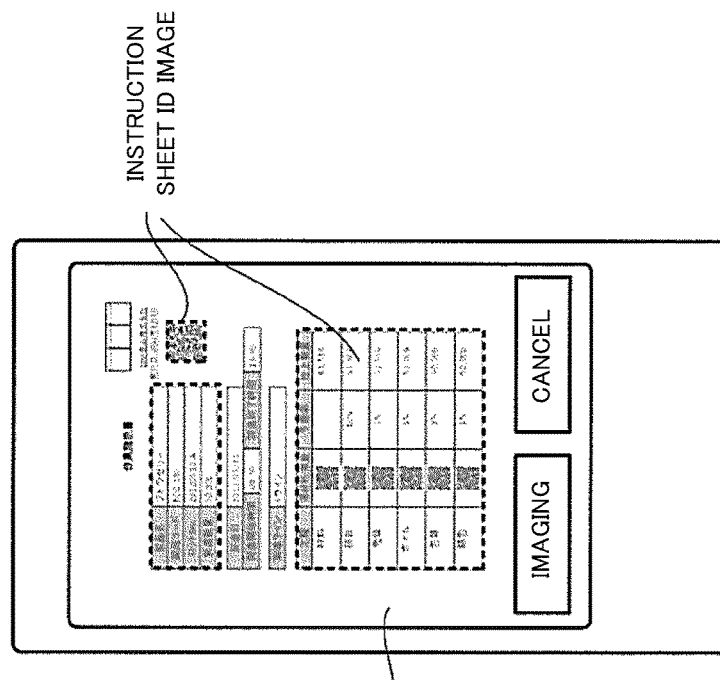
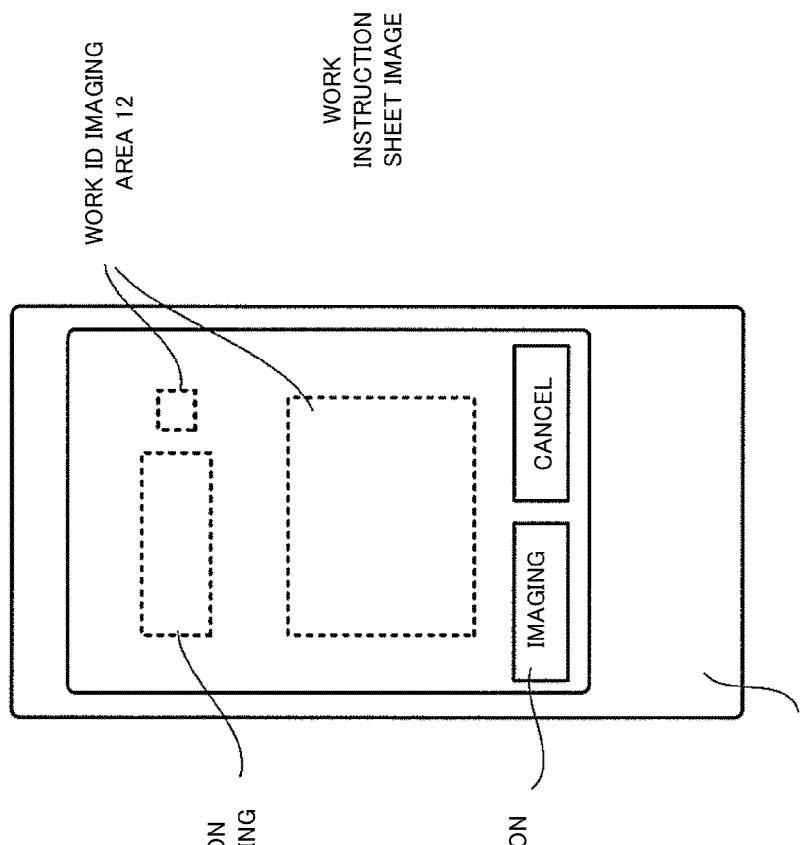
FIG. 7B
FIG. 7A

FIG. 9A
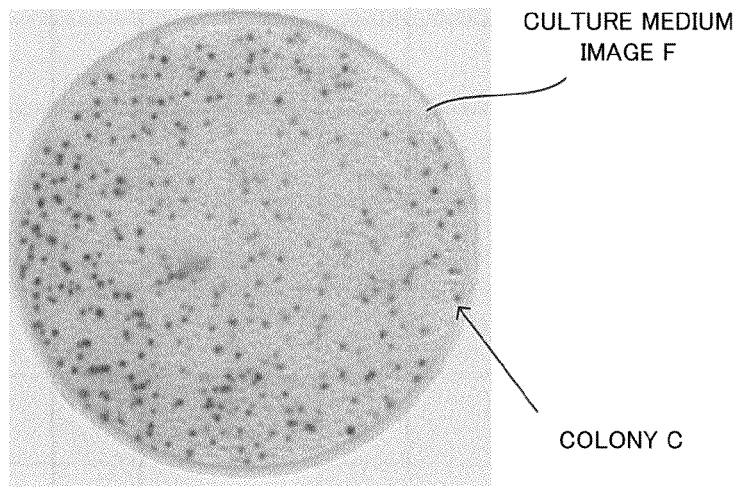
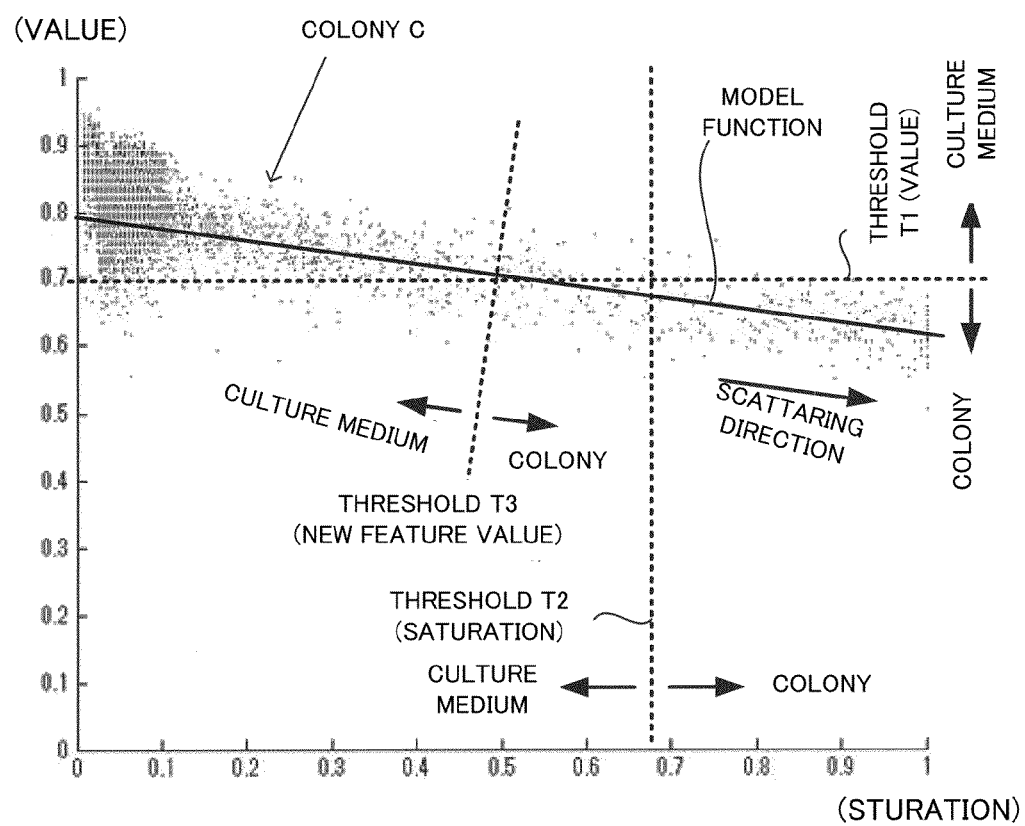
FIG. 9B

GRAY SCALE IMAGE

CULTURE MEDIUM
RECONSTRUCTION IMAGE

RGB COLOR SPACE

HSV COLOR SPACE

PIXEL Pn (Xn,Yn)
CULTURE MEDIUM IMAGE F

LINEAR FUNCTION

NEW FEATURE VALUE
ROTATION

CULTURE MEDIUM INFORMATION REGISTRATION SYSTEM, COLONY DETECTION DEVICE, PROGRAM AND SANITARY MANAGEMENT SYSTEM

TECHNICAL FIELD

The present invention relates to a sanitary management system for food.

BACKGROUND TECHNIQUE

Recently, due to growth of the food service industry such as fast food and increase of easy processed food, opportunity of eating food cooked by others is remarkably increasing. On the other hand, if dangerous substance such as toxic substance or microbe is mixed into foodstuffs such as processed ingredients or processed food, it directly affects the human body. Therefore, in handling the processed food, it is required to strictly manage not only safety of raw material but also sanitation of production process to ensure the safety of food through the whole food processing.

Particularly, beginning from food poisoning cases problematically occurring in various regions, it is a proposition to further improve the safety of food. There are increasing number of companies not only complying with the food sanitation law but also introducing "HACCP (Hazard Analysis Critical Control Point System)" and/or "FSSC (Food Safety System Certification 22000)".

As a system for detecting microorganisms mixed into processed food, there is known a system which uses a film-type culture medium, images specimens cultured on the film-type culture medium and executes image processing of the image of the culture medium thereby to detect and count colonies (For example, Patent Reference 1). Particularly, in case of using value and hue of each pixel constituting the culture medium image, this system detects colonies by analyzing the culture medium image based on brightness of each pixel constituting the culture medium image so as to prevent erroneous detection due to unevenness of imaging environments such as resolution and illuminance as well as culture condition such as kinds of bacteria.

PRIOR ART REFERENCES

Patent References

Patent Reference 1: Japanese Patent Application Laid-open under No. 2011-212013

SUMMARY OF INVENTION

Problem to be Solved by the Invention

However, in Patent Reference 1 mentioned above, it becomes difficult to detect colonies when the difference of brightness is small between the colonies and the culture medium, as well as value and hue, due to kinds of bacteria, a culture environment and an imaging environment.

The present invention is achieved to solve the problem described above, and its object is to provide a culture medium information registration system capable of improving accuracy in detecting the number of colonies and preventing erroneous detection to precisely detect the number of colonies.

Means for Solving the Problem

In order to solve the above problem, the culture medium information registration system according to the present invention comprises: an obtaining unit which obtains culture medium image data including a culture medium image created by imaging a culture medium on which food is cultured as a specimen; an extracting unit which extracts two or more feature values related to a color of each pixel constituting the culture medium image; a calculation unit which executes statistical analysis based on distribution of pixels of the culture medium image by using a coordinate system prescribed by the extracted two or more feature values of each pixel, and calculates a model function prescribing relation of the two or more feature values in each pixel; a detection unit which detects colonies in the culture medium image based on the calculated model function; a count unit which counts a number of detected colonies; and a registration unit which registers information related to the culture medium including at least the counted number of colonies with a database as culture medium information.

Effect of the Invention

The culture medium information registration system, the culture medium detection device, the program and the sanitary management system according to the present invention can improve the accuracy in detecting the number of colonies, and can precisely detect the colonies with preventing erroneous detection. In addition, the culture medium information registration system and the sanitary management system according to the present invention can register accurate culture medium information and precisely execute the sanitary management of food, by improving the accuracy in detecting the number of colonies and precisely detecting the colonies with preventing erroneous detection.

Further, by the culture medium information registration system, the culture medium detection device, the program and the sanitary management system according to the present invention, resources can be saved in comparison with the case of executing and providing various data analysis by using physical resources such as a paper medium, and registration error can be remarkably reduced by registering the culture medium information related to the culture medium with the database. Therefore, difficult management of the culture medium can performed easily, and resources can be saved without wastefully consuming the culture media.

BRIEF DESCRIPTION OF THE DRAWINGS

FIG. 3 is an example of a work instruction sheet used in the sanitary management system of the embodiment.

FIGS. 6A and 6B show examples of the image displayed on the display unit when the film-type culture medium is imaged by the portable communication terminal device of the embodiment.

FIGS. 7A and 7B are examples of the image displayed on the display unit when a work instruction sheet is imaged by the portable communication terminal device of the embodiment.

FIGS. 9A and 9B are diagrams (part 1) for explaining a principle of a conversion processing of feature values of each pixel constituting a culture medium image in an image analysis processing unit of the embodiment.

DETAILED DESCRIPTION OF THE PREFERRED EMBODIMENTS

A Preferred embodiment of the present invention will be described below with reference to the attached drawings. The following embodiment is directed to a case where a culture medium information registration system, a program, a colony detection device and a sanitary management system according to the present invention are applied to a sanitary management system using a film-type culture medium in a production line or an inspection line (hereinafter referred to as "work line") of food. However, the present invention is not limited to the following embodiment within a range including its technical idea.

[1] Sanitary Management System

Figure 1:
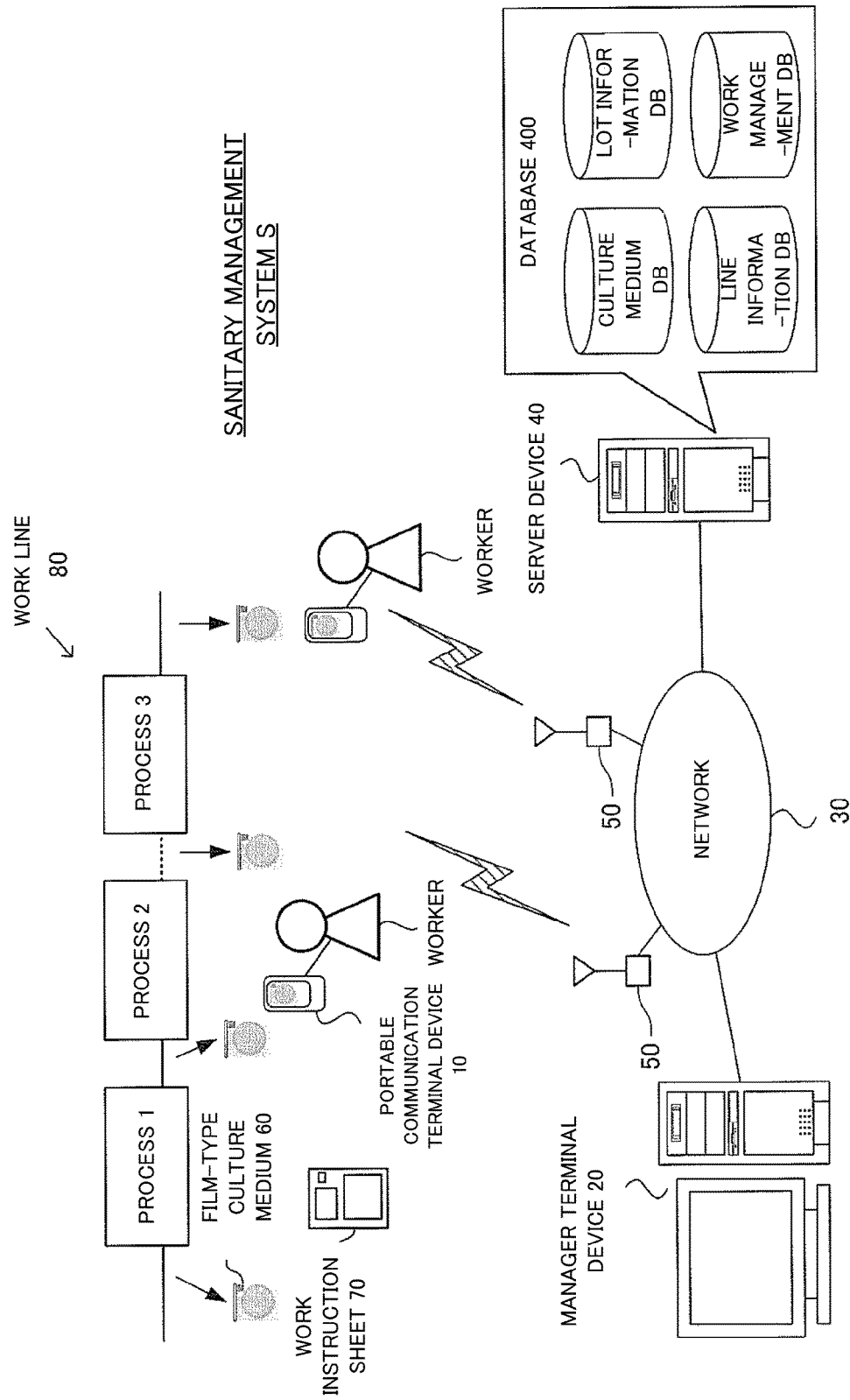
FIG. 1 is a diagram showing a configuration of an embodiment of a sanitary management system according to the present invention.

First, a sanitary management system S according to the embodiment will be described with reference to FIG. 1. FIG. 1 is a block diagram illustrating a configuration of the sanitary management system S of the embodiment.

The sanitary management system S of the embodiment uses a film-type culture medium, and manages information related to the culture medium (hereinafter referred to as "culture medium information") to inspect sanitary condition of food at the time of its production and inspection.

Also, in a work line 80 including the production process for producing food being processed or already processed or the inspection process for inspecting food, the sanitary management system S of the embodiment extracts the food being produced or already produced as a specimen, and executes data management of culture condition of culturing bacteria specified in advance, such as viable microorganisms and coliform bacteria, generated in the specimen in the film-type culture medium 60.

Then, in order to manage and determine the sanitary condition of the food based on the data, the sanitary management system S associates information related to work in the production and inspection of food (hereinafter referred to as "work information") with the culture medium information of the film-type culture medium 60 obtained by a portable communication terminal device 10 before and after culturing bacteria (colony) generatied in the extracted specimen, and registers them with a server device 40 (specifically, a database 400).

Particularly, the sanitary management system S of the embodiment executes image analysis utilizing statistical analysis for the culture medium image obtained by imaging the film-type culture medium 60 after a predetermined time has passed from the start of the culture, and controls the contrast of each pixel constituting the culture medium image (i.e., the contrast in color between the pixels constituting the culture medium and the pixels constituting the colony) to detect the bacteria (colony) generated and cultured in the specimen. Then, the sanitary management system S stores the culture medium information including at least the number of the detected colonies into the database 400.

In order to achieve the configuration described above, as shown in FIG. 1, the sanitary management system S of the embodiment includes a plurality of portable communication terminal devices 10 used to register the culture medium information related to each film-type culture medium 60, a manager terminal device 20 which manages the sanitary management system S, a network 30, and a server device 40 which includes the database 400 and cooperates with the portable communication terminal devices 10 or the manager terminal device 20 to execute various processing including registration management of the culture medium information.

The work information in the embodiment includes information related to the food extracted from the production process or the inspection process as the specimen and the culture of colonies generated in the specimen, in addition to various information related to the production process or the inspection process, and is registered with the database 400 by using unique identification information (hereinafter referred to as "work ID") for each work.

Specifically, each of the work information includes:
(1) Work ID,
(2) Identification information of the work line 80 from which specimen is to be extracted (hereinafter referred to as "line ID"), or the line ID and identification information of the process (hereinafter referred to as "process ID 71b") when the work line 80 includes plural processes,
(3) Product name of the food as the specimen, identification information of the lot (hereinafter referred to as "lot ID") and a name of the lot, (4) Type of bacteria, such as viable microorganism or coliform bacteria, detected from the specimen (hereinafter referred to as "inspection type"), (5) Culture condition of specimen, such as dilution rate, type of diluent, culture temperature, culture humidity and culture time, (6) Culture start time of the specimen, (7) Time after a predetermined time has passed from the start of culture of the specimen (hereinafter referred to as "culture inspection time"), (8) Place of culturing the specimen such as an incubator number and positions of steps in the incubator, (9) Work date and time indicating a start time and an ending time of the work, and

(10) Worker ID (employee ID) and the name of worker. Each information in the work information is registered with the database 400 for each type and for each work.

The portable communication terminal device 10 is a communication terminal device such as a digital camera having a communication function, a tablet-type information terminal device, a smartphone or a mobile phone, which has an imaging or recording function of still pictures (hereinafter referred to as "camera function") and is portable by the worker.

Particularly, the portable communication terminal device 10 images the film-type culture medium 60 by the camera function to generate image data (hereinafter referred to as "culture medium image data"), and images a work instruction sheet 70 to generate the instruction sheet image. Then, the portable communication terminal device 10 obtains the work ID 71 and the culture medium ID 66 from the image data of the work instruction sheet (hereinafter referred to as "instruction sheet image data") and the culture medium image data of the film-type culture medium 60, and registers the work ID 71 and the culture medium ID 66 thus obtained, the culture medium image data and the metadata of the culture medium image data with the database 400 of the server device 40, as the culture medium information.

On the other hand, the portable communication terminal device 10 transmits the culture medium information to the server device 40 directly or via access points 50 by using a short-range wireless communication standard such as BLUETOOTH (Registered Trademark), wireless LAN (WLAN: Wireless Local Area Network) or wireless PAN (WPAN: Wireless Personal Area Network), or by using a public telephone network via a mobile base station not shown. The portable communication terminal device 10 has a browser function configured by a markup language such as XML (eXtensible Markup Language), executes operation input instruction and operation confirmation of the worker by using the browser function, and transmits the culture medium information to the server device 40 via the browser function.

The manager terminal device 20 is an information communication terminal device such as a tablet-type information terminal device, a smartphone, a personal computer or a workstation. The manager terminal device 20 functions as a control device which manages identification information of the manager (hereinafter referred to as "manager ID"), the password of the manager and identification information of the worker (hereinafter referred to as "worker ID"), and executes the management of the access authorization to the server device 40, the management of the terminal IDs of the portable communication terminal devices 10, the correction of the registered culture medium information and other management.

Also, the manager terminal device 20 has the browser function configured by a markup language similarly to the portable communication terminal device 10, and can execute data communication with the server device 40 and browsing of the reports by using the browser function.

The manager terminal device 20 can correct the culture medium information and other information when each work is terminated due to a trouble of a machine executing the process or other reasons in the same lot or when the registration error of the culture medium information is made by the worker.

For example, the network 30 is configured by a public telephone network (hereinafter referred to as "a long distance communication network") including a mobile communication network, an IP (Internet Protocol) network such as a short-range wireless network, or both of them connected to each other. However, the configuration of the network 30 is not limited to them.

The server device 40 is a server device which cooperates with the portable communication terminal device 10 and the manager terminal device 20 to execute data processing for the sanitary management of the lot and the work line 80.

Particularly, the server device 40 cooperates with the potable communication terminal device 10 to execute registration of the culture medium information in each film-type culture medium 60 before starting the culture (hereinafter referred to as "initial registration") and registration after starting the culture (hereinafter referred to as "post-culture registration"). Also, the server device 40 obtains the culture medium information transmitted from the portable communication terminal device 10, and detects colonies generated and cultured on the specimen from the culture medium image formed by the culture medium image data included in the obtained culture medium information.

Basically, in order to detect colonies, the server device 40:

(1) obtains the culture medium image data including the culture medium image generated by imaging the culture medium (from the portable communication terminal device 10), (2) extracts two or more feature values related to the color of each pixel constituting the culture medium image, (3) executes statistical analysis based on the distribution of the pixels of the culture medium image by using a coordinate system prescribed by each of the extracted two or more feature values thereby to calculates a linear function (hereinafter referred to as "model function") prescribing relation of the two or more feature values in each pixel, (4) detects colonies in the culture medium image based on the calculated linear function, (5) counts the number of colonies thus detected, and (6) registers information related to the culture medium including at least the number of colonies thus counted, with the database, as the culture medium information.

Particularly, the server device 40 of the embodiment converts the coordinate values of each pixel in the coordinate space prescribed by the extracted two or more feature values to a new feature value based on the calculated linear function, and detects the colonies in the culture medium image based on the converted new feature value. Specifically, the server device 40 of the embodiment classifies each of the pixels of the culture medium image into the pixels constituting the culture medium (hereinafter referred to as "culture medium pixel") and the pixels constituting the colony cultured in the culture medium (hereinafter referred to as "colony pixel"), and then detects the colonies.

Also, as the statistical analysis, the server device 40 of the embodiment calculates an axis parallel with a scattering direction of each pixels on the coordinate system based on the coordinate values of each pixels prescribed by the two or more feature values in the coordinate system.

Then, the server device 40 of the embodiment executes statistical analysis of regression analysis based on the extracted two or more feature values of each pixel to calculate the regression line as a liner function, or executes statistical analysis of principal component analysis based on the extracted two or more feature values of each pixel to calculate the axis of the first principal component as the linear function.

Further, the server device 40 of the embodiment extracts at least two color components out of the color components of each pixel as the feature values to execute statistical analysis, or obtains plural color components of each pixel and extracts the feature value obtained by converting the color space of the obtained color components as the feature value to execute statistical analysis.

The server device 40 of the embodiment may reconstruct the culture medium image based on a new feature value of each pixel and position information of each pixel on the culture medium image (i.e., generate reconstruction image), and may register the reconstruction image thus generated with the database as the culture medium information.

Also, in this embodiment, the two or more feature values of the color components extracted from each pixel of the culture medium image include each feature value of each RGB color component, hue, value (brightness), saturation and gradation value, and also include feature values obtained by the conversion of the color space such as saturation and value converted from each RGB color components. However, the feature values of the color components indicate "saturation" and "value" in the following description, unless specifically mentioned. The new feature value indicates the feature value related to a new color component calculated by the linear function mentioned above.

With this configuration, in the sanitary management system S of the embodiment, each pixel is distributed in a given coordinate system based on two or more feature values related to the color such as the RGB color components, hue, value (brightness), saturation and gradation value, and the statistical analysis such as the regression analysis or the principal component analysis is executed to calculate the linear function prescribing the relation of the two or more feature values. Therefore, it is possible to obtain the linear function prescribing the color of the colony and the color of the culture medium imaged in the culture medium image by the same function.

Accordingly, in the sanitary management system S of the embodiment, it is possible to eliminate feature values other than the feature values extracted from each pixel constituting the culture medium image and to detect colonies by focusing on the contrast of the image with respect to the extracted feature values. Therefore, it is possible to improve the accuracy in detecting the number of colonies and to precisely detect the colony with preventing erroneous detection.

Particularly, in the sanitary management system S of the embodiment, since the feature values of each pixel can be converted to a new feature value based on the calculated linear function and the contrast can be enhanced between the color of the culture medium and the color of the colony, it is possible to easily and precisely classify the pixels into the colony pixels and the culture medium pixels by using binarization processing or Hough transform, for example.

Also, in the sanitary management system S of the embodiment, since the linear function can be calculated along the scattering direction of each pixel constituting the culture medium image, it is possible to precisely calculate the linear function prescribing the contrast based on the extracted feature values.

Also, in the sanitary management system S of the embodiment, since the linear function can be calculated based on the versatile statistical analysis such as the regression analysis or the principal component analysis, it is possible to easily execute the statistical analysis and the arithmetic operation based on the statistical analysis with a simple configuration.

Also, in the sanitary management system S of the embodiment, since the linear function can be calculated by using not only each RGB color component simply extracted from the pixel constituting the culture medium image but also various color components such as hue and value, it is possible to calculate an appropriate linear function.

Then, in the sanitary management system S of the embodiment, resources can be saved in comparison with the case of executing and providing various data analysis by using physical resources such as a paper medium, and registration error can be remarkably reduced by registering the culture medium information related to the culture medium with the database. Therefore, difficult management of the culture medium can be performed easily, and resources can be saved without wastefully consuming the culture media.

[2] Film-Type Culture Medium

Figure 2:
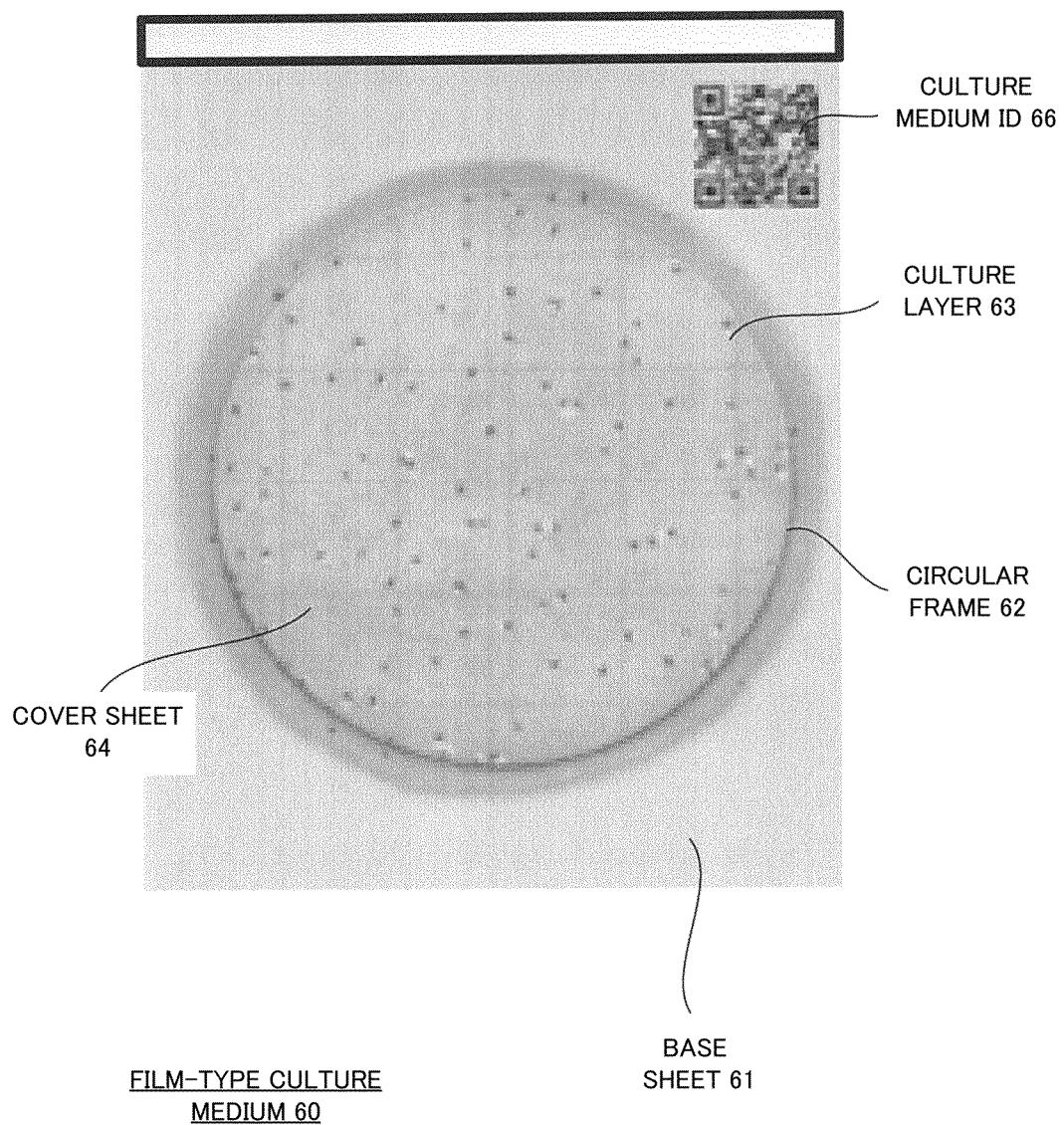
FIG. 2 is an example of a film-type culture medium used in the sanitary management system of the embodiment.

Next, the film-type culture medium 60 of this embodiment will be described with reference to FIG. 2. FIG. 2 is an example of the film-type culture medium 60 used in this embodiment.

The film-type culture medium 60 used in this embodiment is a culture medium to culture bacteria generated in food, serving as a specimen, detected from each process of the work line 80 by a dried culture medium like a film or a sheet. The film-type culture medium 60 is used as a culture medium to culture viable microorganisms, coliform bacteria and Staphylococcus aureus. The film-type culture medium 60 may be used as a culture medium to culture various kinds of bacteria, substance or microorganism such as mold, yeast, Listeria monocytogenes, water microorganism, lactic acid bacteria, and protein.

As shown in FIG. 2, the film-type culture medium 60 includes a base sheet 61 formed of a film, a circular frame (hereinafter referred to as "circular frame") 62 formed on the base sheet 61 from the center of the base sheet 61, a culture layer 63 provided inside the frame and culturing bacteria, a cover sheet 64 to cover the culture layer 63, and a culture medium ID 66 formed on the right side of the base sheet 61.

For example, the culture medium ID 66 is formed as a barcode such as a two-dimensional barcode or alphanumeric characters. The culture medium ID 66 is imaged when the film-type culture medium 60 is imaged, and is recognizable by the analysis of the portable communication terminal device 10 or the server device 40.

The base sheet 61 is a base material of a film or a sheet, and its material is not limited. For example, a plastic film or a paper may be used. Preferably, an example of the plastic film is a resin film such as polyethylene, polypropylene, polyethylene-telephthalate, polyethylene-naphthalate, polymethacrylate, polymethyl methacrylate, polymethyl acrylate, polyester, and polycarbonate. Polyethylene-telephthalate or a synthetic paper of polypropylene is preferred. The synthetic paper of polypropylene is a film synthetic paper mainly made from polypropylene.

The film-type culture medium 60 may include an IC tag storing the culture medium ID 66, and the portable communication terminal device 10 may obtain the culture medium ID 66 by a short-range wireless communication interface 140 (e.g., an IC tag reader) provided in the portable communication terminal device 10.

[3] Work Instruction Sheet

Next, the work instruction sheet 70 of this embodiment will be described with reference to FIG. 3. FIG. 3 is an example of the work instruction sheet 70 used in this embodiment.

The work instruction sheet 70 of this embodiment is an instruction sheet on which work names and contents of one or more production process or inspection process, the work line 80 used, a name of food (processed food) produced or inspected, a quantity and other information are written for each group of food produced or inspected under the same condition, i.e., for each lot.

The work instruction sheet 70 of this embodiment includes an instruction sheet ID 71a formed by printing or other method at the right upper part, and plural process IDs 71b formed by printing or other method at predetermined areas. The instruction sheet ID 71a and each of the process IDs 71b are used as the work ID 71, and is formed by a barcode such as a two-dimensional barcode or alphanumeric characters, for example. The instruction sheet ID 71a and each of the process IDs 71b are imaged when the film-type culture medium 60 is registered, similarly to the culture medium 60, and are recognized by the analysis in the portable communication terminal device 10 or the server device 40.

Similarly to the film-type culture medium 60, the work instruction sheet 70 may include an IC tag storing the work ID which is the instruction sheet ID 71a or the process ID 71b, and the portable communication terminal device 10 may obtain the work ID 71 by an interface (a short-range wireless communication interface 140 described later) such as a tag reader provided in the portable communication terminal device 10. In the following description, the work ID 71 indicates the instruction sheet ID 71a or the process ID 71b, unless specifically mentioned.

[4] Portable Communication Terminal Device

[4.1] Configuration of Portable Communication Terminal Device

Figure 4:
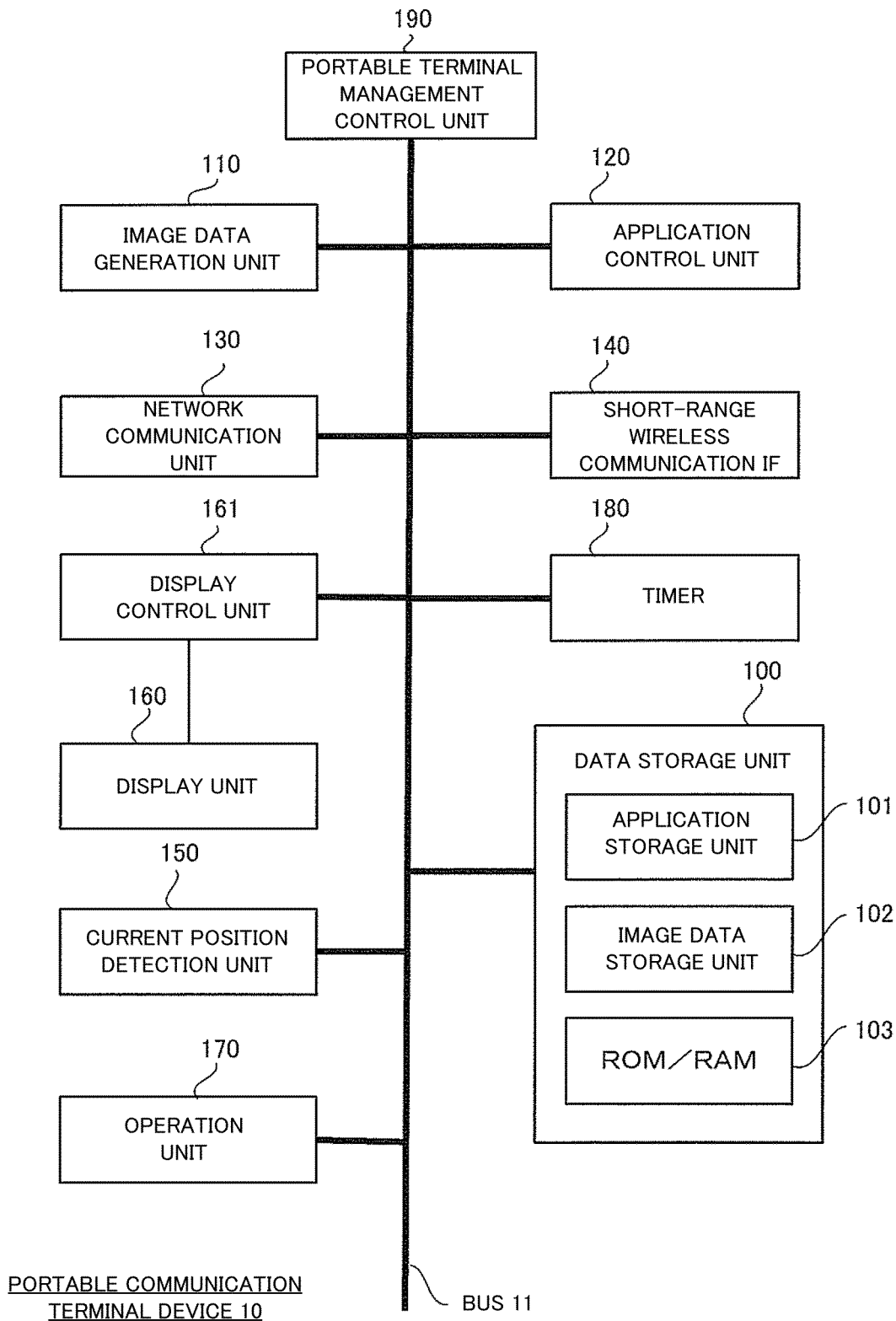
FIG. 4 is a block diagram showing a configuration of a portable communication terminal device used in the sanitary management system of the embodiment.

Next, the configuration of the portable communication terminal device 10 of this embodiment will be described with reference to FIG. 4. FIG. 4 shows the configuration of the portable communication terminal device 10 of this embodiment.

The portable communication terminal device 10 of this embodiment includes a data storage unit 100 which has a memory function used when various programs are executed, an image data generation unit 110 which has an imaging function and which generates the image data of the film-type culture medium 60 and other image data, and an application control unit 120 which cooperates with the server device 40 to execute processing of registering the culture medium information with the server device 40 as the initial registration and after the culture (hereinafter referred to as "culture medium information registration processing") and other processing.

Also, the portable communication terminal device 10 includes a network communication unit 130 which communicates with the server device 40 and other communication device a short-range wireless communication interface 140 which transmits and receives data to and from the IC tag and other communication interface, a current position detection unit 150 which detects the current position, a display unit 160, a display control unit 161 which controls the display unit 160, an operation unit 170 for inputting user's operation, a timer 180, and a portable terminal management control unit 190 which controls the whole device.

For example, if the portable communication terminal device 10 has a telephone function and a mailing function such as an e-mail, it includes various necessary elements such as a microphone, a speaker and an e-mail transmitting/receiving function. Further, each of the above-described units is connected to each other by a bus 11 to transmit and receive data.

The data storage unit 100 includes an application storage unit 101 which stores various application programs, an image data storage unit 102 which stores image data imaged and generated by the image data generation unit 110, and ROM/RAM 103 which stores programs related to the management and control of the portable communication terminal device 10, which is used as a work area during the execution of each program, and which stores data used in each processing executed in the portable communication terminal device 10.

Particularly, the application storage unit 101 stores application programs executed by the application control unit 120 in cooperation with the image data generation unit 110, the operation unit 170, the display control unit 161 and the image data storage unit 102. Also, the application storage unit 101 stores browser program to realize the browsing function described above.

The image data storage unit 102 stores the culture medium image data and the instruction sheet image data, the image ID for managing each image data, various metadata such as the imaging time corresponding to each image data, the work ID 71, the culture medium ID 66 and various flag information, in a manner associated with each other. The image ID is arbitrary identification information suitably given in each of the portable communication terminal devices 10.

The image data generation unit 110 includes an optical system, a CCDI (Charge Coupled Device Image) sensor which converts an optical image inputted from the optical system to an electric signal, and a generation unit which generates the image data based on the electric signal generated by the CCDI sensor.

Particularly, the image data generation unit 110 images the work instruction sheet 70 to generate the instruction sheet image data. Also, the image data generation unit 110 images the film-type culture medium 60 on which the specimens are cultured or being cultured, to generate the culture medium image data of the film-type culture medium 60.

The application control unit 120 realizes culture medium information registration processing executed by a predetermined application. Particularly, the application control unit 120 executes various control programs for controlling each unit of the portable communication terminal device 10 by the culture medium registration application stored in the application storage unit 101, and cooperates with or controls the network communication unit 130, the display control unit 161 and the operation unit 170 to execute various processing.

In view of implementation, the application control unit 120 may be achieved as a function realized when the CPU (Central Processing Unit) constituting the portable terminal management control unit 190 executes the application. The detail of the registration processing of the culture medium information, executed in the application control unit 120 of the embodiment, will be described later.

The network communication unit 130 configures the communication line with the server device 40 connected to the network 30 under the control of the application control unit 120 and the portable terminal management control unit 190, and transmits and receives various data such as the culture medium image data.

The short-range wireless communication interface 140 executes the short-range wireless communication by the IC tag under the control of the application control unit 120 and the portable terminal management control unit 190.

The current position detection unit 150 recognizes the positions of the GPS (Global Positioning System) satellites via the network 30 under the control of the application control unit 120 and the portable terminal management control unit 190, and detects the satellite signals (GPS signals) transmitted from the GPS satellites.

Then, the current position detection unit 150 calculates (i.e., detects) coordinate values indicated by the latitude and longitude of the current position of the portable communication terminal device 10 based on the detected GPS signals. Also, the current position detection unit 150 supplies the calculated coordinate values to the application control unit 120 as the position information.

When the portable communication terminal device 10 has a telephone function or a short-range wireless communication function, the current position of the portable communication terminal device 10 may be calculated (detected) based on the direction and the intensity of the radio wave for the telephone or the short-range wireless communication received by a telephone base station.

The display unit 160, which has an image display area of a predetermined size (e.g., 5 inches, W480×H960 pixels) and is constituted by a panel of a liquid crystal or EL (Electro Luminescence), displays predetermined images based on the display data generated by the display control unit 161. Particularly, in this embodiment, the display unit 160 cooperates with the operation unit 170 to display various information and the image of the work instruction sheet 70 and the film-type culture medium 60 while the culture medium registration application is being executed.

The display control unit 161 generates drawing data necessary to draw a predetermined image on the display device 160 and outputs the generated drawing data to the display unit 160 under the control of the application control unit 120 and the portable terminal management control unit 190.

The operation unit 170 includes various confirmation buttons, operation buttons for inputting each operation instruction, plural keys such as ten-key and a touch sensor provided on the display unit 160, and is used when each operation is performed. Specifically, the operation unit 170 is used to perform the operation for executing various processing described above at the time of activating the culture medium registration application.

In this embodiment, the operation unit 170 may be used when the culture medium ID 66 is directly inputted by hand.

The timer 180 provides the application control unit 120 with the date and time at which the image data generation unit 110 images the film-type culture medium 60.

The portable terminal management control unit 190 is mainly constituted by a central processing unit (CPU) and includes various input/output ports such as a key input port and a display control port. The terminal management control unit 190 totally controls the general function of the portable communication terminal device 10 and the general function to execute the information providing program.

[4.2] Application Control Unit

Figure 5:
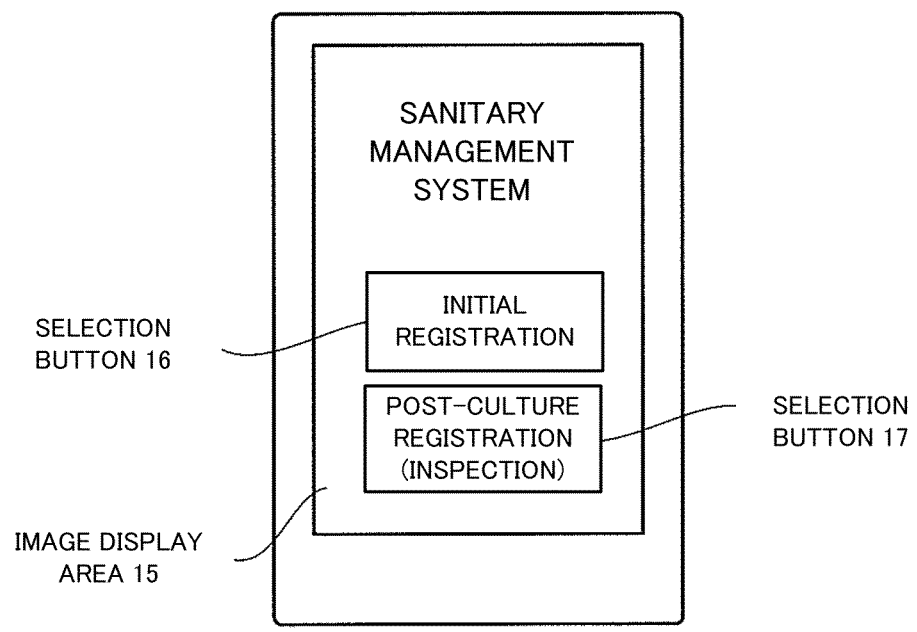
FIG. 5 is an example of an image displayed on a display unit when culture medium information is registered by the portable communication terminal device of the embodiment.

Next, the configuration of the application control unit 120 in the portable communication terminal device 10 of this embodiment will be described with reference to FIGS. 5 to 7. FIG. 5 is an example of an image displayed on the display unit 160 when the portable communication terminal device 10 of this embodiment registers the culture medium information. FIGS. 6A and 6B are examples of images displayed on the display unit 160 when the portable communication terminal device 10 of this embodiment images the film-type culture medium 60, and FIGS. 7A and 7B are examples of images displayed on the display unit 160 when the portable communication terminal device 10 of this embodiment images the work instruction sheet 70.

The application control unit 120 executes the culture medium registration application stored in the application storage unit 101, controls the image data generation unit 110 to obtain the culture medium image data of the film-type culture medium 60, and stores it in the image data storage unit 102.

Then, the application control unit 120 obtains the culture medium ID 66 from the culture medium image data by using an image analyzing function such as a barcode recognition function or an OCR (Optical Character Recognition) function, and stores the culture medium image data, the metadata of the culture medium image data and various flag information into the image data storage unit 102 together with the culture medium ID 66 thus obtained. The application control unit 120 may execute the barcode recognition or the OCR recognition in cooperation with another communication device or a database via a communication line.

Also, after imaging the culture medium image data or at a predetermined timing, the application control unit 120 executes initial registration which registers the culture medium information with the server device 40 at the time of starting the culture of specimen and post-culture registration which registers the culture medium information after starting the culture of the specimen. Particularly, the application control unit 120 specifies the initial registration or the post-culture registration based on the instruction by the worker, and transmits the information (flag information) indicating one of the initial registration and the post-culture registration to the server device 40 in a manner included in the culture medium information.

Also, at the time of imaging the film-type culture medium 60, the application control unit 120 obtains the current time from the timer 180, stores the current time in the image data storage unit 102 as the imaging time together with a predetermined image ID as the metadata of the culture medium image data, and transmits it to the server device 40 together with the culture medium image data transmitted to the server device 40.

For example, as shown in FIG. 5, the application control unit 120 makes the worker who registers the culture medium information select one of the initial registration and the post-culture registration, by detecting the touch on the display of the selection buttons 16 and 17 and the corresponding area of the image display area 15.

When the culture medium ID 66 is formed by a two-dimensional barcode, the application control unit 120 displays the area for imaging the culture medium (hereinafter referred to as "the culture medium imaging area") 27 at the center of the display unit 160 and the area for imaging the culture medium ID 66 (hereinafter referred to as "the culture medium ID imaging area") 18, as shown in FIGS. 6A and 6B, so as to invite the worker to image. Then, the application control unit 120 makes the image data generation unit 110 image the culture medium image having the culture medium ID 66 based on the instruction of the worker (i.e., upon detecting the touch on the imaging button 19).

Further, when the application control unit 120 obtains the data of the work instruction sheet 70 on which the instruction sheet ID 71*a* or the process ID 71*b* is formed by the two-dimensional barcode as the work ID 71, the application control unit 120 displays the area for imaging the instruction sheet ID 71*a* or the process ID 71*b* (hereinafter referred to as "the work ID imaging area") and the area for imaging the work instruction sheet 70 (hereinafter referred to as "instruction sheet imaging area") 13 on the display unit 160, as shown in FIGS. 7A and 7B, so as to invite the worker to image. Then, the application control unit 120 makes the image data generation unit 110 image the work instruction sheet 70 having the work ID 71 based on the instruction of the worker (i.e., upon detecting the touch on the imaging button).

Also, when obtaining the instruction sheet image, the application control unit 120 recognizes the work ID 71 from the instruction sheet image by the image analysis to store the work ID 71 in the image data storage unit 102 together with the culture medium image data, and transmits the work ID 71 to the server device 40 at the time of transmitting the culture medium image data.

At this time, when the process ID 71*b* is obtained as the work ID 71 and plural process IDs 71*b* are formed, the application control unit 120 makes the worker select one of the process IDs 71*b* and obtains the corresponding process ID 71*b*. However, the application control unit 120 may cooperate with the server device 40 to make the worker refer to the line related information and obtain the process ID 71*b* to be obtained based on the instruction of the worker.

When the culture medium ID 66 and the work ID 71, which is the instruction sheet ID 71*a* or the process ID 71*b*2, are stored in the IC tag, the application control unit 120 cooperates with the operation unit 170, the display control unit 161 and the short-range wireless communication interface 140 to obtain the culture medium ID 66 and the work ID 71.

Also, when the server device 40 recognizes the culture medium ID 66 and the work ID 71 from the culture medium image data and the instruction sheet image data, the application control unit 120 transmits the instruction sheet image data as the culture medium information in addition to the culture medium image data.

[5] Server Device

[5.1] Configuration of Server Device

Figure 8:
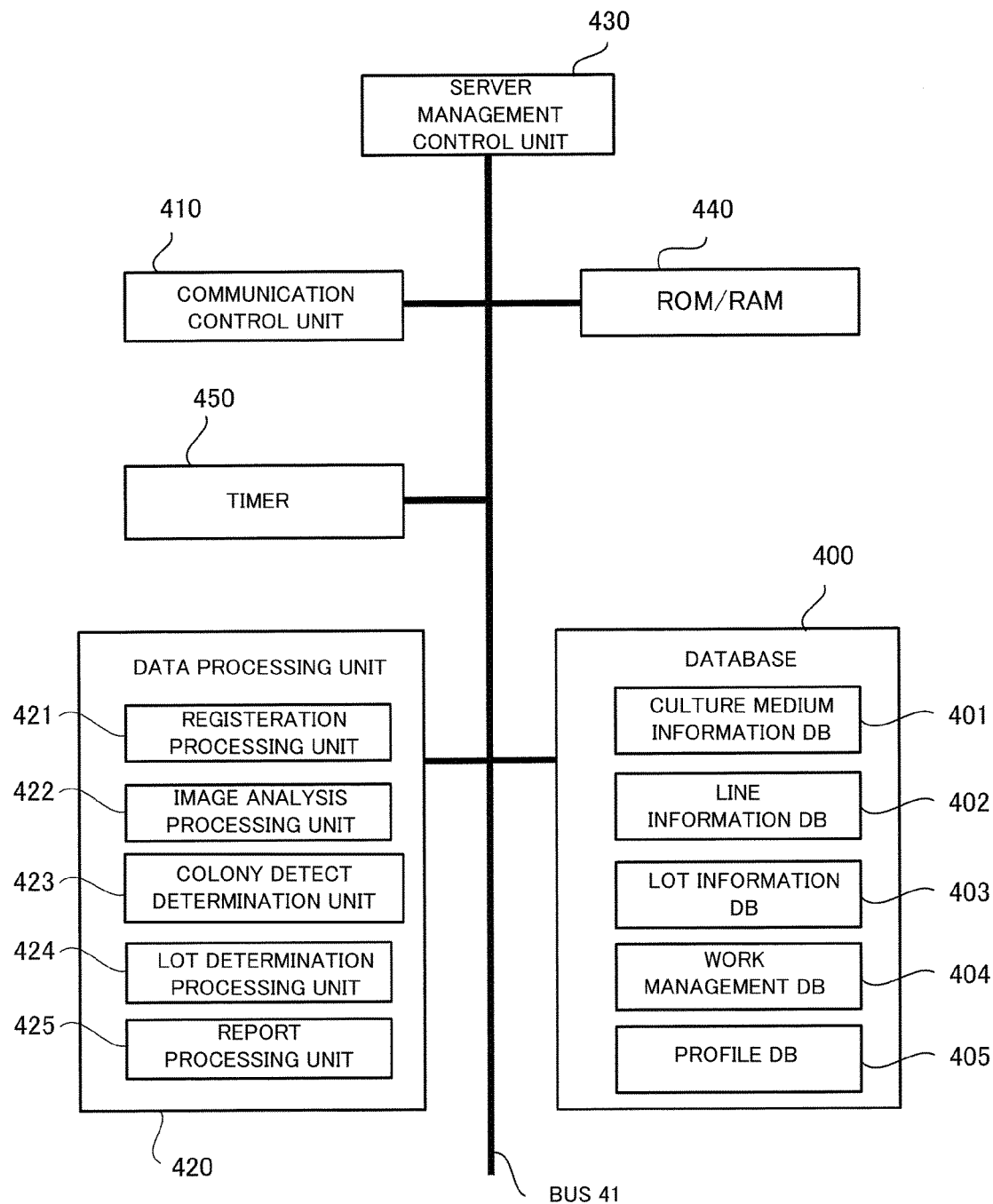
FIG. 8 is a block diagram showing a configuration of a server device used in the sanitary management system of the embodiment.

Next, a configuration of the server device 40 of this embodiment will be described with reference to FIG. 8. FIG. 8 is a diagram showing a configuration of the server device 40 of this embodiment.

As shown in FIG. 8, the server device 40 of this embodiment includes a database 400 which stores various information such as the work information and the culture medium information; a communication control unit 410 which communicates with the portable communication terminal device 10 and the manager terminal device 20; a data processing unit 420 which executes various processing such as the culture medium information registration processing; a server management control unit 430 which controls each unit of the server device 40; ROM/RAM 440 used for the control of each unit; and a timer 450 used for the time management. Each unit described above is mutually connected by a bus 41 to execute data transfer between each constitutive element.

The communication control unit 410 is a predetermined network interface, which configures a communication network with the portable communication terminal device 10 or the manager terminal device 20, and transmits and receives various data to and from the portable communication terminal device 10 or the manager terminal device 20.

The database 400 is formed by a HDD, and includes a culture medium information database (hereinafter referred to as "culture medium DB") 401, a line information database (hereinafter referred to as "line information DB") 402, a lot information database (hereinafter referred to as "lot information DB") 403, a work management database (hereinafter referred to "work management DB") 404 and a profile database (hereinafter referred to as "profile DB"). For example, each DB in this embodiment constitutes the database of the present invention.

The culture medium information DB 401 stores the culture medium information related to the film-type culture medium 60 of the specimen extracted in each process of each work line 80, for each work ID 71 and the culture medium ID 66. For example, the culture medium information DB 401 stores the following data in correspondence with each other.

(1) Culture medium ID
(2) Culture medium image data (or data of culture medium reconstruction image (hereinafter referred to as "culture medium reconstruction data"))
(3) Imaging time
(4) Other information including flag information
(5) A number of colonies
(6) Culture medium determination result
(7) Work ID In a case where the specimen to be extracted is constantly extracted from the same process in the same work line 80 in the same lot, the work ID 71 may be the lot ID. In a case where the specimen to be extracted is extracted from the different work line 80 or the different process in the same lot, the work ID 71 is the line ID or the process ID 71*b*.

Also, the number of colonies and the culture medium determination result in each culture medium information may be registered at the time when the culture medium information is registered, or may be registered at the predetermined timing different from the timing of registering the culture medium information.

Further, in a case where plural imaging time are registered for the culture medium information of the same film-type culture medium 60 (i.e., in a case where there are plural culture inspection time described later), each culture medium information including the culture medium image, the imaging time, the number of colonies and the culture medium determination result is stored for each culture medium inspection time in the same culture medium ID 66.

The line information DB 402 stores the line information related to each work line 80 for each line ID. For example, the line information DB 402 stores the following data in correspondence with each other.

(1) Line ID
(2) Process ID 71*b* of the process in the work line 80 and its type.

As the process type, the name specifying each process including material charging, mixing, boiling, wrapping and packing is used.

The lot information DB 403 stores the lot information related to each lot for each lot ID. For example, the lot information DB 403 stores the following data in correspondence with each other.

(1) Lot ID (Instruction sheet ID 71*a*)
(2) Line ID of the work line used for production or inspection of the lot
(3) Work start time of the lot
(4) Work end time of the lot
(5) Work party of the workers who perform the work of the lot The work management DB 404 stores various information related to the work contents. For example, the work management DB 404 stores the following data in correspondence with each other.

(1) Work ID (2) Line ID of the work line from which specimen is to be extracted (or line ID and Process ID 71b)

(3) Type of specimen (food) (Product name, lot ID and/or lot name)

(4) Inspection type (type of bacterium to be detected, such as viable microorganisms or coliform bacteria)

(5) Culture condition (dilution rate, type of diluent, culture temperature, culture humidity and culture time)

(6) Culture start time (7) Time when a predetermined time has passed after starting the culture (hereinafter referred to as "the culture inspection time")

(8) Culture place (e.g., incubator number and position such as the step number in the incubator)

(9) Work date and time (work start time and work end time), and

(10) Worker ID (and/or worker's name).

As the culture inspection time, a single time (i.e., an ending time for ending the culture of the specimen) may be set, or plural time after passing a statutory or predetermined time from the culture start time, e.g., 24 hours, 48 hours or 72 hours after the culture start time may be set.

The data processing unit 420 executes various data processing in accordance with the application stored in the ROM/RAM 440. Particularly, the data processing unit 420 executes a predetermined program to execute:

(1) operation management of the communication control unit 410, (2) culture medium registration processing in cooperation with each portable communication terminal device 10, (3) conversion processing which executes the image analysis of the culture medium image data to convert the feature values in each pixel of the culture medium image, while calculating the linear function serving as the basis, (4) colony detection determination processing which detects the number of colonies based on the converted feature value of each pixel, (5) lot determination processing which determines the lot based on the registered culture medium information, (6) report processing which outputs the determination result in a form of a report, and (7) management and control of the database 400.

Specifically, the data processing unit 420 includes a registration processing unit 421, an image analysis processing unit 422, a colony detection determination unit 423, a lot determination processing unit 424 and a report processing unit 425.

For example, the registration processing unit 421 of this embodiment constitutes an obtaining unit and a registration unit, and the image analysis processing unit 422 constitutes an extracting unit, a calculation unit and an image generation unit. For example, the colony detection determination unit 423 constitutes a detection unit and a count unit of the present invention. Further, the registration processing unit 421, the colony detection determination unit 423, the lot determination processing unit 424 and the report processing unit 425 will be described later in detail.

The server management control unit 430 is mainly constituted by a central processing unit (CPU), and executes programs for an integrated control of each unit in the server device 40. Specifically, the server management control unit 430 executes login processing of each user based on the login request from the portable communication terminal device 10 by the user's operation, and performs other various controls.

The ROM/RAM 440 stores various programs necessary for the operation of the server device 40. Particularly, the ROM/RAM 440 stores the determination criterion information (hereinafter referred to as "culture medium determination criterion information") used to execute the culture medium determination (acceptance/rejection determination), the process determination, the line determination and the lot determination for each film-type culture medium 60. Also, the ROM/RAM 440 is used as a work area during the execution of each program.

The timer 450 is used to manage necessary time when the registration processing of the culture medium information and the lot determination information are executed.

[5.2] Registration Processing Unit

Next, the detail of the registration processing unit 421 in the server device 40 of this embodiment will be described.

The registration processing unit 421 cooperates with the portable communication terminal device 10 to execute the registration processing for registering the culture medium information with the culture medium information DB 401, in correspondence with the work ID 71. Particularly, the registration processing unit 421 executes different culture medium information registration processing based on the flag information included in the culture medium information and indicating one of the initial registration and the post-culture registration.

(Initial Registration)

When the flag information indicating the initial registration is included in the culture medium information transmitted from the portable communication terminal device 10, the registration processing unit 421 executes the registration processing based on the initial registration.

Specifically, when the registration processing unit 421 obtains the culture medium information via the communication control unit 410, it specifies the culture medium ID 66 and the work ID 71 included in the culture medium information. The registration processing unit 421 searches the work management DB 404 based on the specified work ID 71 to specify the corresponding work information, and registers the obtained culture medium image data and the imaging time with the culture medium information DB 401 in correspondence with the specified work information.

Particularly, the registration processing unit 421 specifies the lot ID including the work line 80 from which the specimen is extracted, the line ID of the work line 80 and the process ID 71b in which the specimen is extracted, based on the obtained work ID 71, and registers the culture medium image data and the imaging time included in the culture medium information with the culture medium information DB 401 in correspondence with the lot ID, the line ID and the process ID 71b thus specified.

Then, the registration processing unit 421 registers the imaging time with the culture medium information DB 401 as the culture start time. On the premise that the registration processing of the culture medium information is executed at the time, a preset time may be used as the culture start time, instead of the imaging time.

(Post-Culture Registration)

When the flag information indicating the post-culture registration is included in the culture medium information transmitted from the portable communication terminal device 10, the registration processing unit 421 executes the registration processing based on the post-culture registration.

Specifically, when the registration processing unit 421 obtains the culture medium information via the communication control unit 410 similarly to the initial registration, it specifies the culture medium ID 66 and the work ID 71 included in the culture medium information. Then, the registration processing unit 421 searches the work management DB 404 based on the specified work ID 71 to specify the corresponding work information, and registers the imaging time with the culture medium information DB 401 in correspondence with the specified work information. Similarly to the culture start time, a preset time may be used as the culture inspection time on the premise that the registration processing of the culture medium information is executed at that time.

On the other hand, the registration processing unit 421 makes the image analysis processing unit 422 analyze the obtained culture medium image data to convert the feature values of each pixel of the culture medium image while calculating the linear function serving as a basis. Then, the registration processing unit 421 makes the colony detection determination unit 423 detect the colonies and count the number of colonies based on the feature values of each pixel thus converted, and determine acceptance/rejection of the specimen on each film-type culture medium 60 based on the number of colonies. Also, the registration processing unit 421 registers the culture medium information, including the detected number of colonies and the determination result, with the culture medium information DB 401 in correspondence with the specified work ID 71.

The registration processing unit 421 may register the culture medium image data as the culture medium information, or may register the data of the reconstructed image obtained by reconstructing the culture medium image by the linear function calculated as the determination criterion, as described later.

[5.3] Image Analysis Processing Unit

[5.3.1] Principle of Conversion Processing of Feature Values in Each Pixel

First, the description will be given of a principle of conversion processing of the feature values of each pixel constituting the culture medium image by the image analysis processing unit 422 of the embodiment with reference to FIGS. 9 to 12. FIGS. 9 to 11 are diagrams for explaining the principle of the conversion processing of the feature values of each pixel constituting the culture medium image by the image analysis processing unit 422 of the embodiment, and FIG. 12 is an example of a gray scale image and an image of a new feature value in the film-type culture medium 60.

Under the control of the registration processing unit 421, the image analysis processing unit 422 of the embodiment:

(1) obtains the culture medium image from the culture medium image data included in the culture medium information transmitted from the portable communication terminal device 10, (2) extracts two or more feature values related to the color of each pixel constituting the obtained culture medium image, (3) executes the statistical analysis based on the distribution of pixels of the culture medium image by using the coordinate system prescribed by each of the extracted two or more feature values of each pixels, and calculates the linear function prescribing the relation of the two or more feature values in each pixel, and (4) converts the coordinate values of each pixel in the coordinate space prescribed by the extracted two or more feature values of each pixel into the new feature value based on the calculated linear function.

Normally, in case of executing the image processing to detect colonies from the culture medium image, information of coloring, size and bleeding of colonies to be detected, information of background color, or information serving as a basis of detecting colonies such as the imaging environment information (hereinafter referred to as "profile") are frequently used. If such information is not or cannot be applied, it is difficult to precisely detect colonies. Namely, it is difficult to precisely classify the imaged film-type culture medium into colonies and the culture medium other than the colonies (i.e., background) by a simple binarization processing, causing detection error of colonies with high possibility.

On the other hand, in a case where colonies are cultured on the culture medium such as the film-type culture medium 60, the color of the colonies appearing on the pixel is the color changed from the color of the culture medium when observed in view of the color component such as saturation or value. Therefore, in consideration of state transition of each pixel, the color change from the color of the culture medium to the color of the colony can be approximated by a function whose feature value is uniquely determined.

Figure 10A:
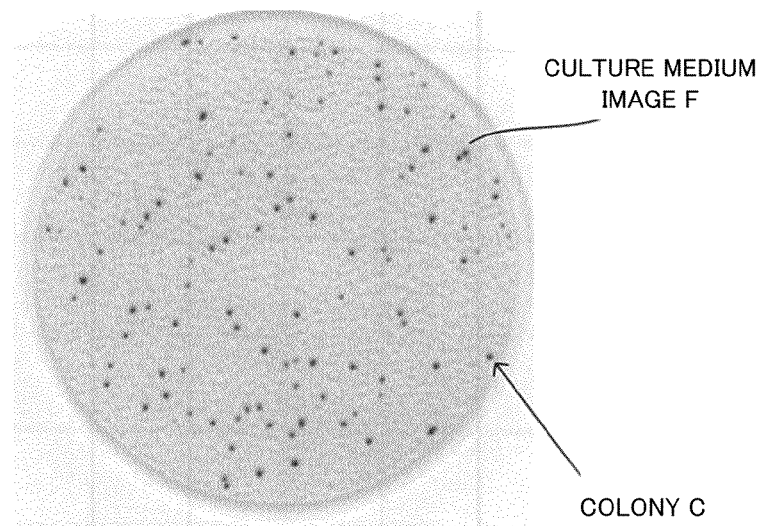
FIGS. 10A and 10B are diagrams (part 2) for explaining a principle of a conversion processing of feature values of each pixel constituting a culture medium image in an image analysis processing unit of the embodiment.
Figure 10B:
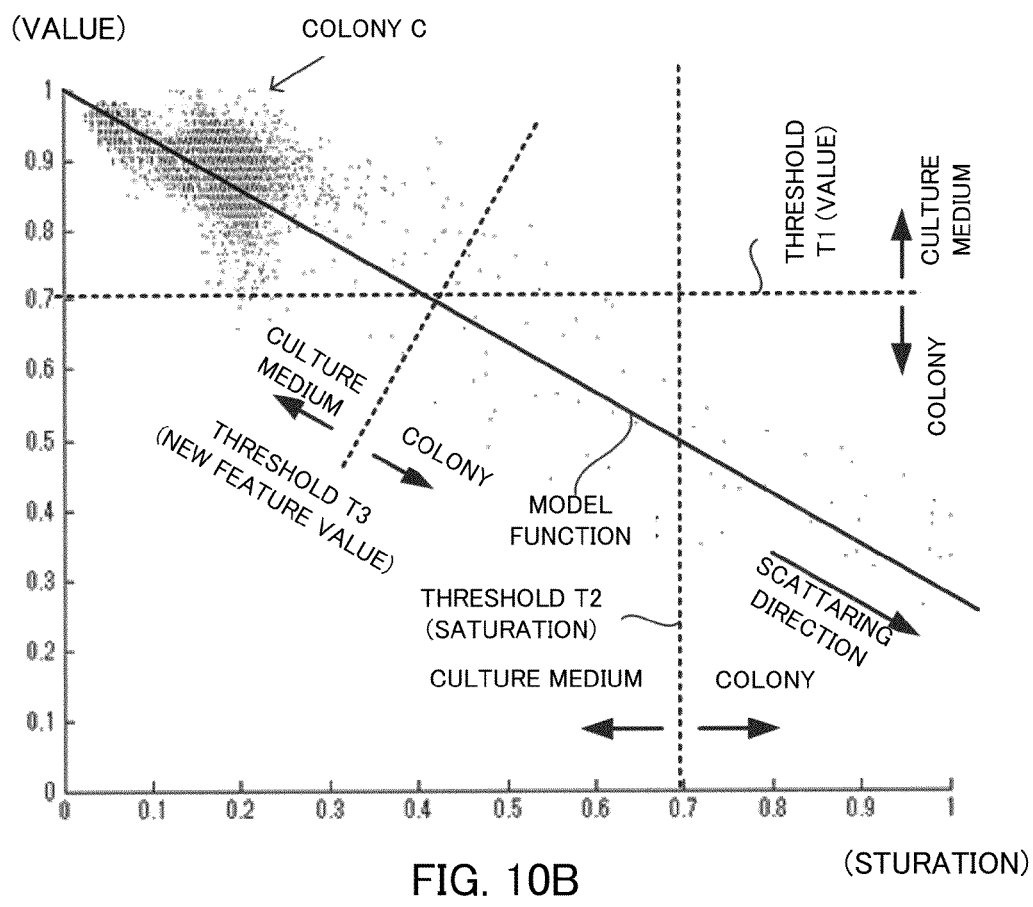
Figure 11A:
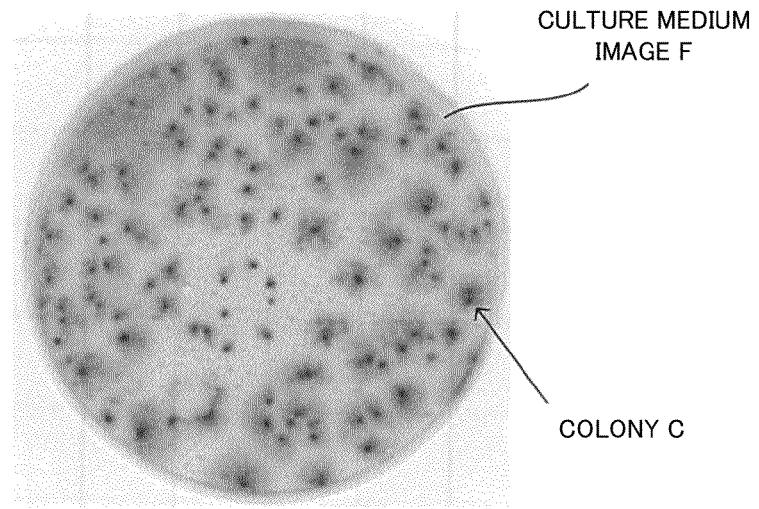
FIGS. 11A and 11B are diagrams (part 3) for explaining a principle of a conversion processing of feature values of each pixel constituting a culture medium image in an image analysis processing unit of the embodiment.
Figure 11B:
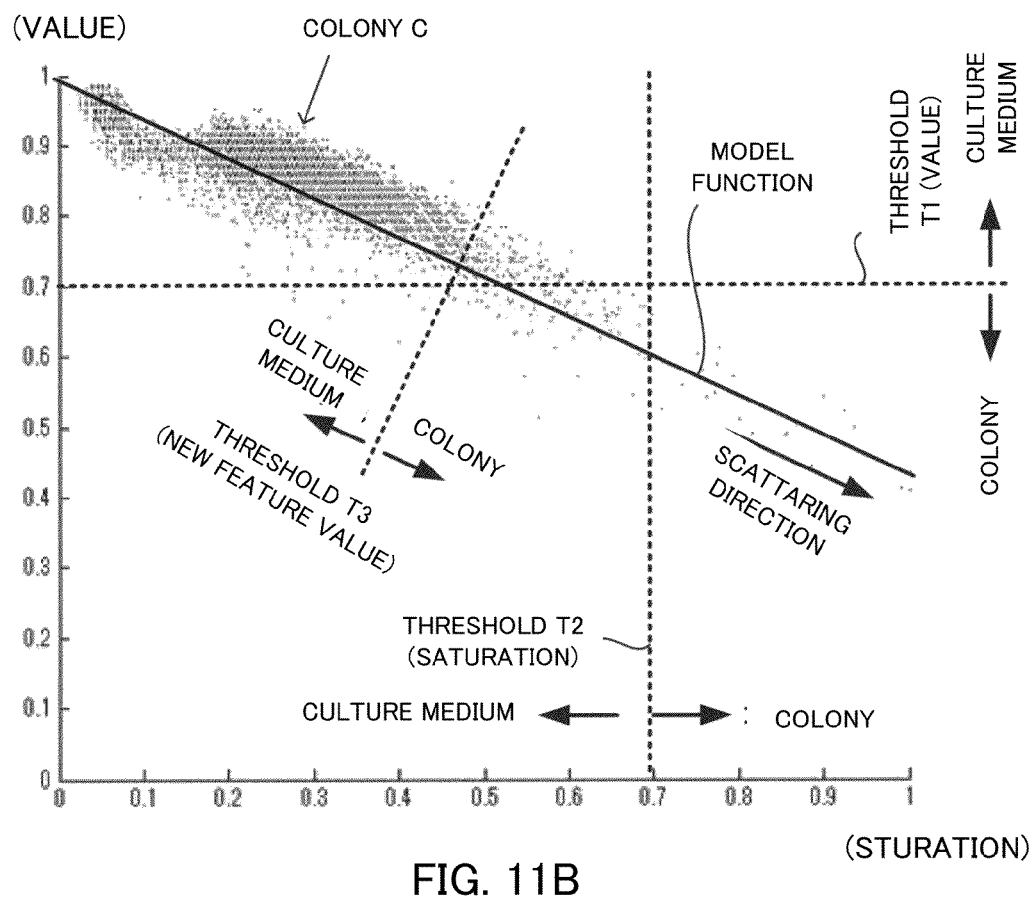

Also, in a case where the culture medium image F shown in FIG. 9A, FIG. 10A or FIG. 11A is obtained and each pixel value P of the culture medium image F is simply binarized by saturation or value, the distribution direction of the feature values is different according to the culture medium as understood from the scatter diagrams shown in FIG. 9B, 10B or 11B. Therefore, it is not always possible to precisely separate the colony and the background based on the existing criterion of saturation or hue (threshold "T1" or "T2") for various culture medium images. On the other hand, since each pixel has two standard colors, i.e., the colony color and the background color in the coordinate system based on saturation and value, each pixel scatters in a predetermined direction on the coordinate system. Thus, the axis parallel with the scattering direction of each colony is presumed to be a model function (specifically, a linear function) changing from the colony color to the background color.

Therefore, the image analysis processing unit 422 of the embodiment eliminates the feature values other than the extracted feature values based on two or more feature values related to the color, such as each RGB color component, hue, value (brightness), saturation and gradation value, calculates the linear function prescribing both colors of the colony and culture medium imaged on the culture medium image by the same function, and converts the feature values of the color components of each pixel constituting the culture medium image into a new feature value based on the linear function thus calculated.

Figure 12A:
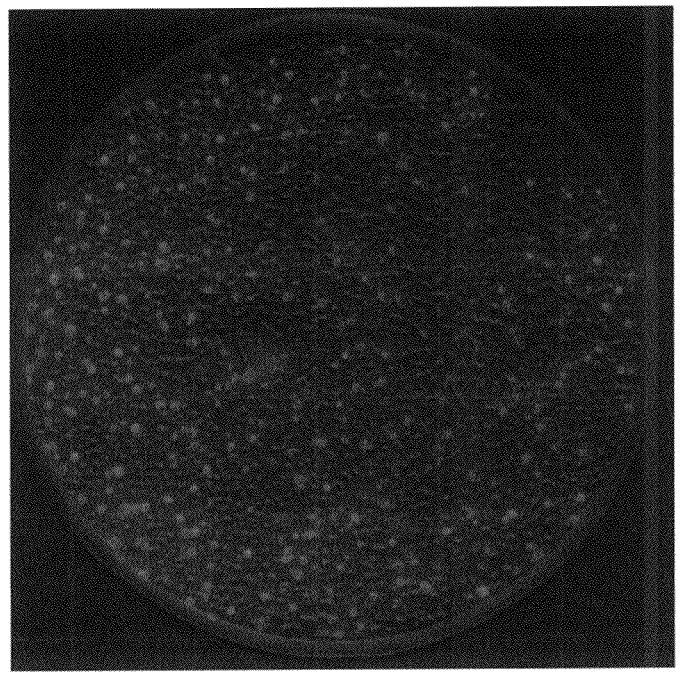
FIGS. 12A and 12B are examples of a gray scale image and a culture medium image (a culture medium reconstruction image) of a new feature value in a film-type culture medium.
Figure 12B:
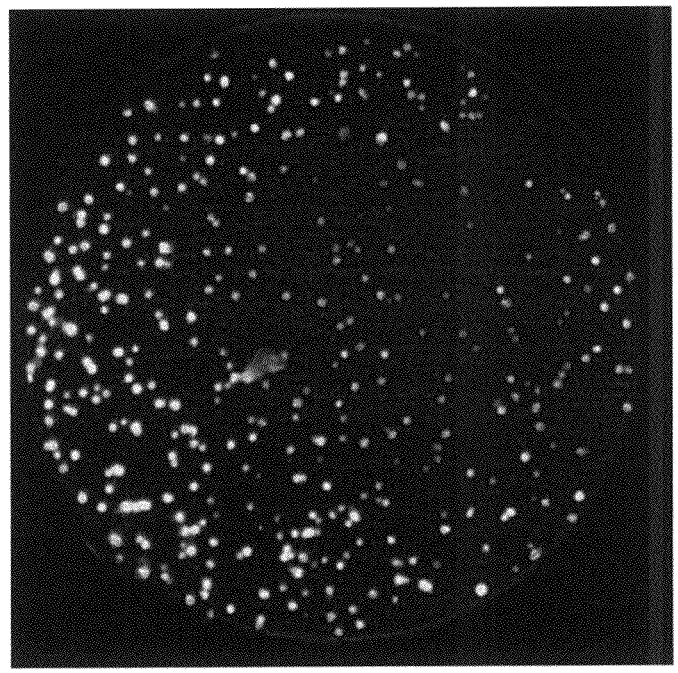

For example, when the culture medium image shown in FIG. 9A is obtained, the image analysis processing unit 422 constructs the gray scale image simply constituted by the brightness value of each pixel as shown in FIG. 12A as the image used for the basis of detecting colonies. However, when a new feature value is calculated from the feature values of the color components of each pixel shown in FIG. 9B, 10B or 11B (e.g., T3 in FIG. 9B, 10B or 11B) by using the linear function (model function) calculated by executing the above-mentioned processing and the culture medium image F is reconstructed by using the calculated feature value as the brightness value, it is possible to generate the culture medium image (culture medium reconstruction image) in which the contrast of the color component is adjusted as shown in FIG. 12B. Namely, the distance on the linear function thus calculated becomes the newly-defined feature value of the color, and when the feature value is imaged based on the new feature value of each pixel calculated by the linear function and its position information on the culture medium image as described later, it is possible to generate the culture medium reconstruction image having high contrast ratio for a certain color component as shown in FIG. 12B.

By detecting colonies imaged based on each pixel prescribed by the new feature value, the colony color (specifically, the colony pixel) and the background color (specifically, the culture medium pixel) can be precisely classified, and hence it is possible to precisely detect colonies from the culture medium.

While a linear function is used as the "model function" for the explanation in this embodiment, the model function is not limited to a straight line and may be a function expressing a curved line such as a function of a curved line having small curvature or a function including the curved line, or a function having a curved part. In this case, for example, statistical analysis such as multiple regression analysis capable of obtaining a quadratic function may be executed. Alternatively, based on the distribution density of pixels or other factors, another function obtained for a partial segment may be synthesized with the linear function obtained by the regression analysis or the principal component analysis.

[5.3.2] Specific Processing in Image Analysis Processing Unit

Next, the specific processing in the image analysis processing unit 422 of the embodiment will be described with reference to FIGS. 13 and 14. FIG. 13 is a diagram for explaining the feature values of the color component extracted in the image analysis processing unit 422, and FIG. 14 is a diagram for explaining the linear function calculated in the image analysis processing unit 422.

(Extracting Feature Values)

The image analysis processing unit 422 obtains plural color components of R (Red), G (Green) and B (Blue) of each pixel constituting the culture medium image obtained from the culture medium image data, and converts each value of the obtained color components in the color space (RGB color space) into the saturation and value (also referred to as "brightness", but "value" is used in this embodiment. In this embodiment, the gradation value in the gray scale is referred to as "brightness".) in the HSV color space.

Specifically, the image analysis processing unit 422 obtains the gradation values (e.g., 0 to 255) in each RGB color component for each pixel, and calculates the saturation S and the value V in the HSV color space by the equations (1) and (2) to extract them as the feature values of color components of each pixel. In the equations (1) and (2), "MAX" indicates the maximum value of the RGB gradation values in each pixel, and "MIN" indicates the minimum value of the RGB gradation values in each pixel.

$$\text{Saturation } S = (MAX - MIN)/Max \quad (1)$$

$$\text{Value } V = MAX \quad (2)$$

Figure 13A:
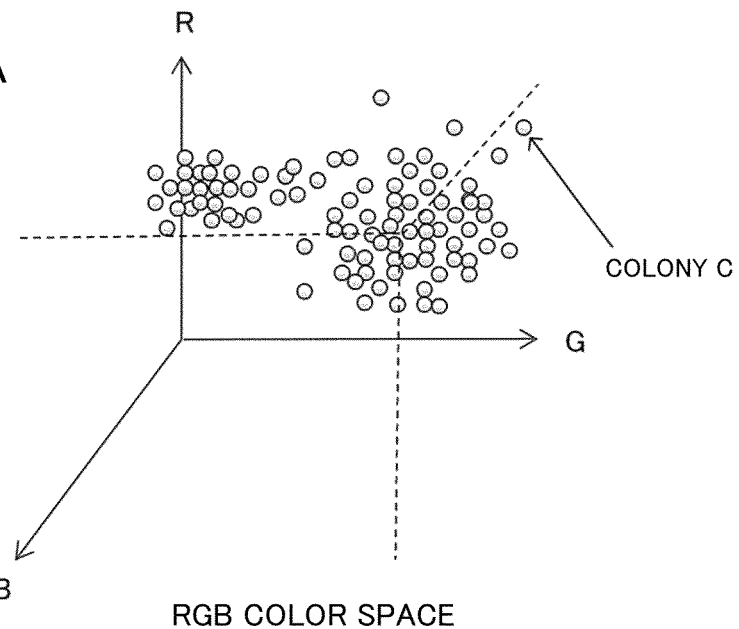
FIGS. 13A and 13B are diagrams for explaining feature values of color components extracted in the image analysis processing unit of the embodiment.
Figure 13B:
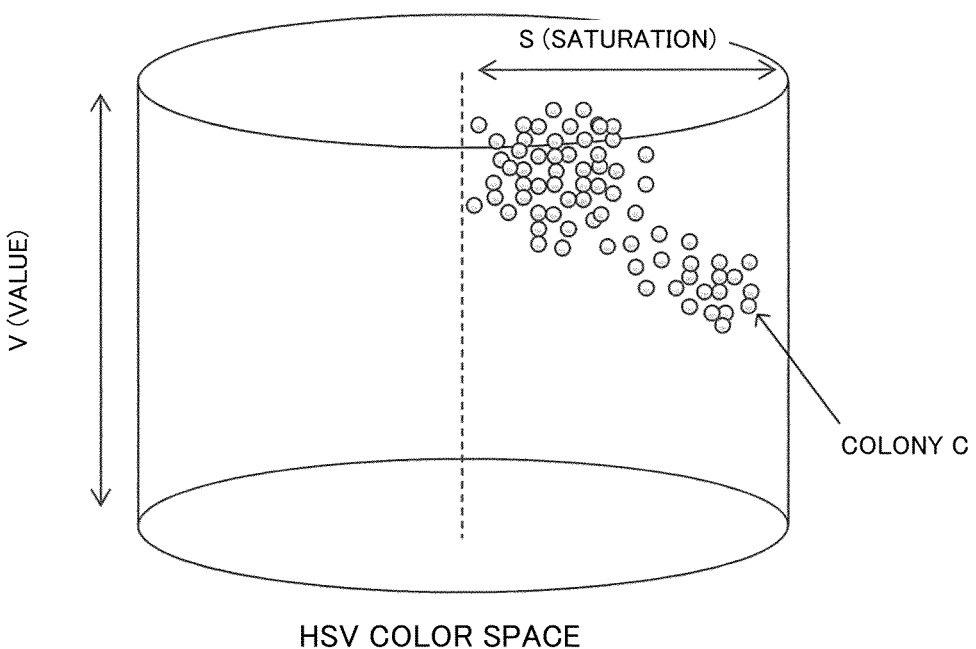

For example, in a case where the culture medium image shown in FIG. 10A is obtained, the image analysis processing unit 422 converts each pixel from each of the RGB gradation values in the RGB color space shown in FIG. 13A to each value in the HSV color space shown in FIG. 13B, and extracts the saturation and the value thus converted as the feature values.

(Calculating Linear Function Based on Statistical Analysis)

As described above, the image analysis processing unit 422 executes mapping of all the pixels of the culture medium image on the color feature value space having the coordinate system prescribed by the saturation and the value of each extracted pixel, executes the statistical analysis of its distribution, and calculates the linear function prescribing the relation of two or more feature values in each pixel.

Specifically, as the statistical analysis, the image analysis processing unit 422 calculates the axis parallel with the scattering direction of each pixel on the coordinate system as the linear function based on the coordinate values $(Xn, Yn) = (Sn, Vn)$ in the coordinate system of each pixel prescribed by the saturation S and the value V. Here, "n" indicates the number (ID) of each pixel constituting the culture medium image.

Particularly, as the statistical analysis, the image analysis processing unit 422 of the embodiment executes the regression analysis or the principal component analysis on the distribution of pixels mapped in the color feature value space of the two-dimensional coordinate system prescribed by the feature values of the saturation and value, and calculates the regression line or the axis of the first principal component as the linear function.

Specifically, in case of executing the regression analysis as the statistical analysis, the image analysis processing unit 422 performs the squares method to execute the regression analysis based on the plural pairs of the coordinate values prescribed by the saturation and value of each pixel, and calculates the linear model function as the linear function for converting the coordinate values of each pixel to the new feature value.

Figure 14A:
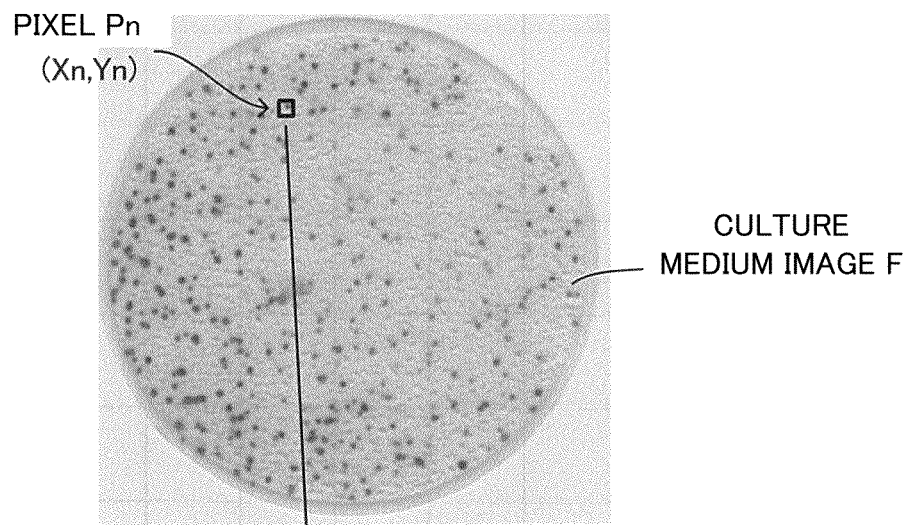
FIGS. 14A to 14C are diagrams for explaining a linear function calculated in the image analysis processing unit of the embodiment.
Figure 14B:
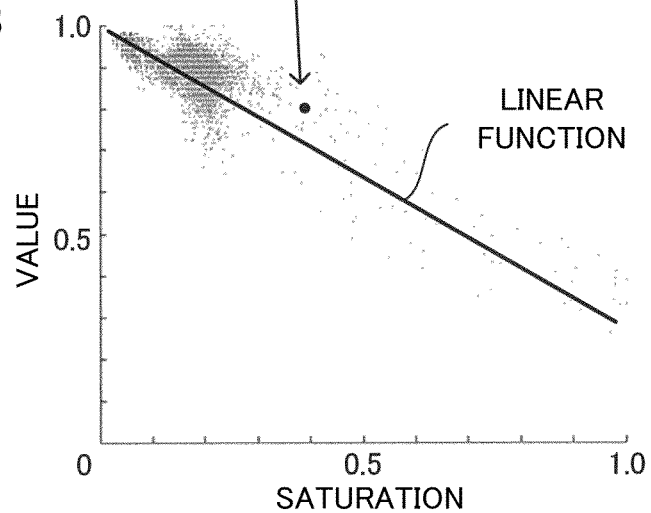

Namely, when obtaining the culture medium image shown in FIG. 14A, the image analysis processing unit 422 plots each pixel $Pn(Xn, Yn)$ on the scatter diagram based on the saturation and value as shown in FIG. 14B, and executes the operation processing equivalent to calculating the straight line A parallel with the scattering direction, by the least squares method, from the scatter diagram in which each pixel P is plotted.

When the coordinate value prescribed by the saturation and value of each pixel is distributed on the two-dimensional coordinate system, the axis which is parallel with the scattering direction of the pixels and along which the scattering is most broadly spreading is presumed to be the model function at the time of changing from the colony color to the background color. Accordingly, the straight line calculated by the least squares method, by which the sum of the squares of the coordinate point of each pixel and the residual becomes the minimum, is parallel with the scattering direction and most appropriately fits the spreading direction of the distribution. Therefore, the image analysis processing unit 422 can calculate the model function which is the regression line, by the least squares method, as the linear function which prescribes both the colony color and the culture medium color imaged on the culture medium image by the same function.

On the other hand, when executing the principal component analysis as the statistical analysis, the image analysis processing unit 422 executes the principal component analysis based on the plural pairs of the coordinate values prescribed by the saturation and value of each pixel, and calculates the axis of the first principal component as the model function which is the linear function for converting the coordinate values of each pixel to the new feature value.

In the principal component analysis, the axis which is parallel with the scattering direction of the pixel and along which the scattering is most widely spreading becomes the principal component of the vector. Therefore, the image analysis processing unit 422 can calculate the model function which is the axis of the first principal component as the linear function for projectively converting each pixel.

However, the principal component analysis is such an analyzing method that can express the distribution of quantitative data by many variables by a smaller number of new indexes and that largely gives the influence of the part at which the distribution of the pixels is concentrated. Thus, if the number of pixels of the background or the colony becomes large, there may be a case where the axis of the first principal component does not coincide with the scattering direction. Therefore, when the image analysis processing unit 422 determines that the distribution of the pixels is concentrated, it extracts a predetermined number of pixels from the part to execute the principal component analysis.

(Conversion to New Feature Value)

Figure 14C:
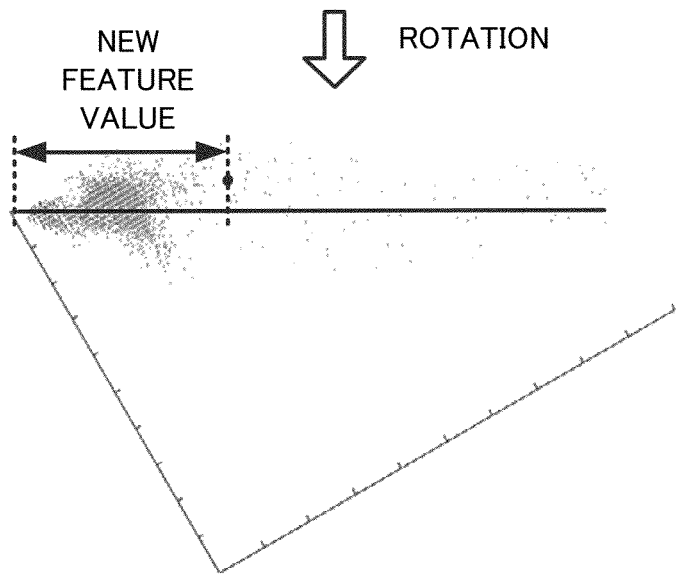

The image analysis processing unit 422 converts the coordinate values on the two-dimensional coordinate system of the saturation and value of each pixel constituting the culture medium image to the new feature value based on the calculated linear function. For example, as shown in FIG. 14C, the image analysis processing unit 422 rotates the coordinate values of each pixel P by a rotation matrix by using the calculated linear function as the reference axis to calculate the new feature value.

Since the new feature value is the value Y (the distance from the intercept of Y-axis) prescribed by the distance on the axis of the linear function, the image analysis processing unit 422 may simply calculate the distance on the linear function as the new feature value, or may projectively convert the coordinate values of each pixel on the axis of the linear function to calculate the new feature value.

[5.3.3] Application Examples (Generating Culture Medium Reconstruction Image)

The image analysis processing unit 422 generates the culture medium reconstruction image based on the calculated new feature value and the position information of each corresponding pixel on the culture medium image. Thus, by generating the culture medium reconstruction image by the new feature value, the image analysis processing unit 422 can generate the culture medium reconstruction image as shown in FIG. 12S, in which the contrast between the colors of the culture medium and the colonies is adjusted in comparison with FIG. 12A.

(Use of Other Color Space)

While the saturation and value are used as the feature values for calculating the linear function, i.e., as the axis of the two-dimensional coordinate system in this embodiment, RGB color components may be used as the feature values and the linear function may be calculated in the RGB three-dimensional coordinate system (i.e., RGB color space). Alternatively, the linear function may be calculated by using two or more color components in Lab color space, which is prescribed by the lightness and complementary colors calculated from the RGB color components similarly to the embodiment.

[5.4] Colony Detection Determination Unit

Next, the detail of the colony detection determination unit 423 in the server device 40 of this embodiment will be described.

The colony detection determination unit 423 of the embodiment detects the colonies generated on the imaged specimen based on the new feature value calculated by the image analysis processing unit 422, counts the number (the number of colonies), and executes the determination as to whether the specimen in each film-type culture medium 60 is normal or abnormal in view of sanitary management, based on the number of colonies thus detected.

Specifically, the colony detection determination unit 423 classifies the colony pixels and the culture medium pixels to detect the colonies, based on the new feature value of each pixel calculated in the image analysis processing unit 422 and a given threshold.

(Detecting Number of Colonies)

The colony detection determination unit 423 executes the detection of the colonies and counting of the number of the colonies based on the new feature value of each pixel and the position information of each pixel constituting the culture medium image, at the time of registering the culture medium information with the culture medium information DB 401 or at a predetermined timing, under the control of the registration processing unit 421, and supplies the number of colonies to the registration processing unit 421.

Specifically, the colony detection determination unit 423 detects pixels whose feature value is equal to or larger than a given threshold value, based on the new feature value of each pixel (hereinafter referred to as "pixel value"). The threshold value may be determined based on reference information predetermined based on rule of thumb or experimental results, or may be determined based on the maximum value and minimum value or the intermediate value on the linear function in the coordinate values of the pixel. Also, the threshold value may be set based on the instruction by the worker or the manager.

Also, the colony detection determination unit 423 executes the image filtering processing to reduce noise. For example, the colony detection determination unit 423 executes the expansion processing which replaces all the pixels neighboring the pixel detected (hereinafter referred to as "the detected pixel") with the detected pixel when there exists another detected pixel neighboring to the detected pixel, and executes the contraction processing which replaces all the pixels neighboring a non-detected pixel when there exists the non-detected pixel neighboring to the detected pixel.

Then, the colony detection determination unit 423 executes labeling which connects the neighboring detected pixel with the pixel recognized as the detected pixel by the image filter processing, recognizes the connected group of the detected pixels as one object i.e., a colony, and calculates the centroid of each recognized colony to detect the number of coordinates as the number of colonies. Additionally, the colony detection determination unit 423 supplies the detected number of colonies to the registration processing unit 421.

While the colony detection determination unit 423 of the embodiment classifies the colony pixels and the culture medium pixels by executing the binarization processing based on the new feature value of each pixel, the detection of the colonies and counting the colonies may be executed by Hough transform which detects a single colony by detecting the edge of the colony based on the new feature value of each pixel and the position information of constituting the culture medium image, by graph theory which prescribes energy function related to the feature value of each pixel to optimize the connection of each pixel (i.e., determination as the same pixel), or by processing of Watershade, level Set or else.

(Acceptance/Rejection Determination of Specimen)

The colony detection determination unit 423 executes the culture medium determination as to whether the specimen in each film-type culture medium 60 is normal or abnormal (i.e., the acceptance/rejection determination of the specimen). For example, the registration processing unit 421 determines the acceptance/rejection of each specimen based on the threshold value (i.e., the criterion) of number of bacteria predetermined for each type of bacterium to be detected from the specimen, and supplies the result to the registration processing unit 421.

Particularly, since the criterion is different based on the bacterium type and/or the dilution rate in this embodiment, the registration processing unit 421 reads out the culture medium determination criterion information from the ROM/RAM 440 based on the criterion of culturing the specimen and the bacterium type to execute the culture medium determination.

Each determination criterion information is specified in correspondence with the culture medium ID 66. Namely, since the type of the film-type culture medium 60 is different between the types of bacteria detected from the specimen, the type of bacterium to be detected can be specified by specifying the culture medium ID 66. Accordingly, in this embodiment, the determination criterion information specified based on the culture medium ID 66 can be read out by predetermining the dilution rate.

Also, in this embodiment, since the acceptance/rejection determination of each film-type culture medium 60 is used in the process determination, the line determination and the lot determination, the culture medium determination is executed in correspondence with each of those determination. The method of determining the acceptance/rejection of each film-type culture medium 60 in the process determination, the line determination and the lot determination will be described later.

[5.5] Lot Determination Processing Unit

Figure 15:
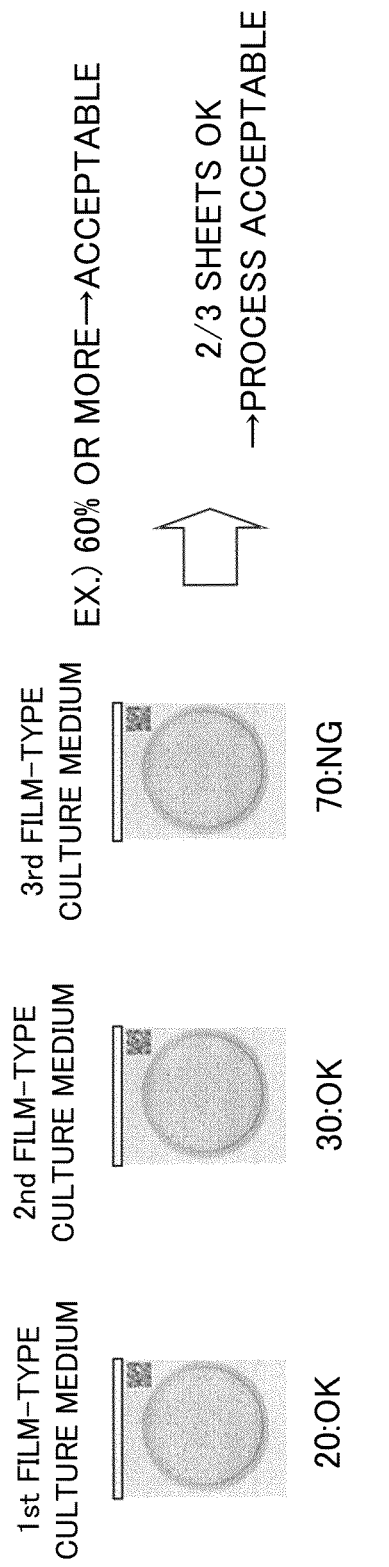
FIG. 15 is a diagram (part 1) for explaining a process determination in the server device of the embodiment.
Figure 16:
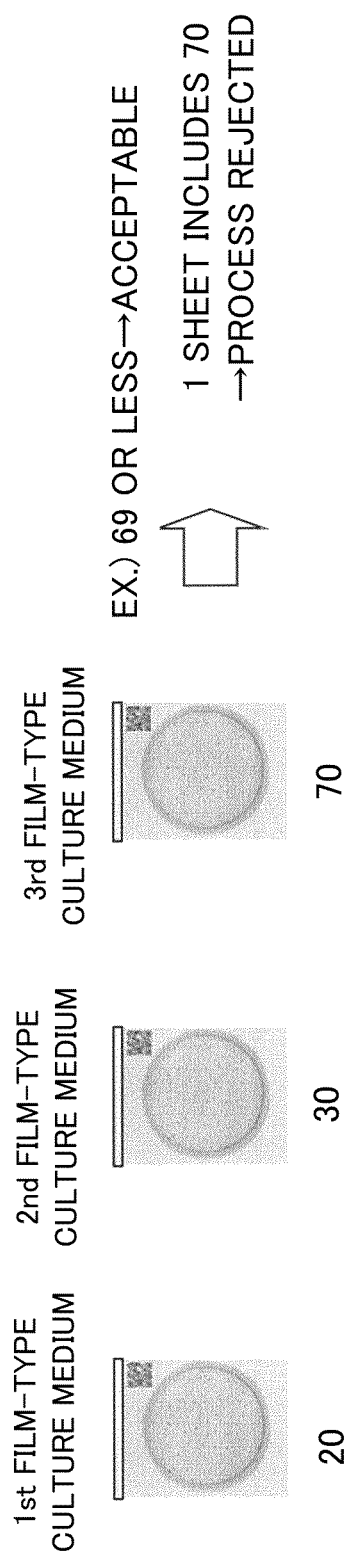
FIG. 16 is a diagram (part 2) for explaining the process determination in the server device of the embodiment.
Figure 17:
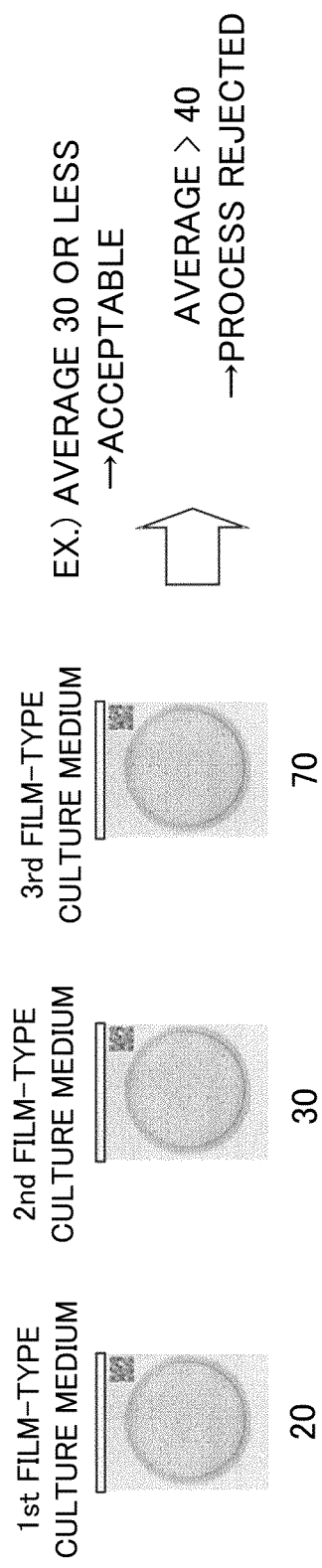
FIG. 17 is a diagram (part 3) for explaining the process determination in the server device of the embodiment.

Next, the detail of the lot determination processing unit 424 in the server device 40 of this embodiment will be described with reference to FIGS. 15 to 17. FIGS. 15 to 17 are diagrams for explaining the process determination in the server device 40 of this embodiment.

The lot determination processing unit 424 of this embodiment executes data analysis related to the sanitary management in the lot, the work line 80 or the process designated (i.e., the acceptance/rejection determination), based on the instruction of the manager inputted to the manager terminal device 20.

Specifically, the lot determination processing unit 424 determines whether or not the food group produced or inspected under the same condition satisfies a predetermined condition, for each lot, based on the line information of the work line 80 used for the corresponding lot and the culture medium information (at least the number of colonies) registered in correspondence with the corresponding work line 80.

Also, when the lot determination is instructed, the lot determination processing unit 424 executes the line determination of the work line 80 which determines whether or not the work line 80 included in the corresponding lot and the process belonging to the work line 80 are normal or abnormal in view of the sanitary management (i.e., the acceptance/rejection determination of the sanitary management) and the process determination of each process (i.e., the acceptance/rejection determination of sanitary management), and executes the lot determination using the process determination and the line determination.

Particularly, when the lot determined is instructed, the lot determination processing unit 424 determines the acceptance/rejection of the process in view of the sanitary management based on the number of colonies in the film-type culture medium 60 in the culture medium information after a predetermined culture inspection time such as 24 hours, 48 hours passed from the start of the culture and the culture medium information of the acceptance/rejection of the specimen, determines the acceptance/rejection of the work line 80 in view of the sanitary management based on the acceptance/rejection determination of the process included in the corresponding work line 80, and determines the acceptance/rejection of the lot in view of the sanitary management based on the acceptance/rejection determination of the work line 80 included in the corresponding lot.

The lot determination processing unit 424 of this embodiment may execute, not the lot determination, but only the process determination or the line determination as the data analysis.

(Process Determination)

The lot determination processing unit 424 executes each process determination based on the culture medium information of plural film-type culture media 60, whose culture start time or the culture inspection time has a predetermined condition, (e.g., the culture start time of the same timing, the culture inspection time of the same timing, the culture start time within the time period from the first time to the second time set in advance, or the culture inspection time within the time period from the first time to the second time set in advance,) and registered in correspondence with the process in the same lot. Namely, the lot determination processing unit 424 executes each process determination by a total determination based on each culture medium determination result of the plural film-type culture media 60.

Specifically, the lot determination processing unit 424 obtains the culture medium determination result of the corresponding film-type culture medium 60 (i.e., all the culture medium determination results registered in the culture medium information having the process ID 71*b* of the process for which the process determination should be executed). The lot determination processing unit 424 determines that the process to be determined is acceptable when the number of the acceptance/rejection determination results satisfies the predetermined condition, and determines that the process to be determined is rejected when the number of the acceptance/rejection determination results does not satisfy the predetermined condition.

For example, as shown in FIG. 15, it is assumed that three film-type culture media 60 have the process ID 71*b* of the process to be determined, the number of colonies of the first film-type culture medium 60 is "20", the number of colonies of the second film-type culture medium 60 is "30", the number of colonies of the third film-type culture medium 60 is "70", the determination results in acceptable when the number of colonies is equal to or smaller than "30", and the predetermined condition is that the process is determined to be acceptable if the process includes the acceptable culture medium information of "60%". In this case, two determination results of three film-type culture media 60 are acceptable, and therefore the lot determination processing unit 424 determines that this process is acceptable.

Also, instead of the above method, the lot determination processing unit 424 may execute the process determination of the process to be determined based on the number of colonies included in the culture medium information having the process ID 71*b* of the process for which the process determination is to be executed.

For example, as shown in FIG. 16, it is assumed that three film-type culture media 60 have the process ID 71*b* of the process to be determined, the number of colonies of the first film-type culture medium 60 is "20", the number of colonies of the second film-type culture medium 60 is "30", the number of colonies of the third film-type culture medium 60 is "70", and the predetermined condition is that the process is determined to be acceptable if the process includes no culture medium information whose number of colonies is equal to or larger than the threshold of the number of colonies "70". In this case, the third film-type culture medium has the number of colonies "70", and therefore the lot determination processing unit 424 determines that this process is rejected.

On the other hand, instead of the above process determination method using the threshold of the number of colonies, the lot determination processing unit 424 may execute the process determination of the process to be determined based on the number of the colonies included in all the culture medium information having the process ID 71*b* of the process for which the process determination is to be executed.

For example, as shown in FIG. 17, it is assumed that three film-type culture media 60 have the process ID 71*b* of the process to be determined, the number of colonies of the first film-type culture medium 60 is "20", the number of colonies of the second film-type culture medium 60 is "30", the number of colonies of the third film-type culture medium 60 is "70", and the predetermined condition is that the process is determined to be acceptable if the average of all the numbers of colonies is equal to or smaller than the threshold "30". In this case, the average of the numbers of the colonies of three third film-type culture media 60 is "40", and therefore the lot determination processing unit 424 determines that this process is rejected.

On the other hand, at the time of executing the process determination, the lot determination processing unit 424 may weight the predetermined process based on the position and/or role, and execute the process determination in consideration of the weight.

Specifically, the lot determination processing unit 424 gives a large weight to the determination result of the process position such as the most downstream process (final process), and gives a large weight to the determination result of the process which sterilize the detected bacteria, such as boiling or burning.

For example, in the case of FIG. 15, the lot determination processing unit 424 executes the process determination with doubling the acceptance/rejection determination result of the film-type culture medium 60 in the most downstream process. Namely, in this case, the lot determination processing unit 424 assumes that it inspects two third film-type culture media 60 and obtains the same value, and determines that the process is acceptable if the acceptance rate of the four film-type culture media 60 is equal to or larger than 60%. For example, in the case of FIG. 15, two determination results out of four film-type culture media 60 are acceptable, and therefore the lot determination processing unit 424 determines that the process is rejected.

Also, in the case of FIG. 16, the lot determination processing unit 424 executes the process determination with setting the threshold value at the time of determining the acceptance/rejection of the film-type culture medium 60 in the most downstream process to ½. Namely, in this case, the threshold of the number of colonies serving as the acceptance/rejection criterion in the third film-type culture medium 60 becomes ½, and the lot determination processing unit 424 determines that the process is acceptable if the number of colonies is smaller than the threshold value in all the three film-type culture media 60. For example, in the case of FIG. 16, the threshold of the third film-type culture medium 60 is "35" and the number of colonies is larger than the threshold. Therefore, the lot determination processing unit 424 determines that the process is rejected.

Further, in the case of FIG. 17, the lot determination processing unit 424 executes the process determination with setting the threshold value at the time of determining the acceptance/rejection of the film-type culture medium 60 in the most downstream process to twice. Namely, in this case, the threshold of the number of colonies serving as the acceptance/rejection criterion in the third film-type culture medium 60 becomes twice, and the lot determination processing unit 424 determines that the process is acceptable if the average of the number of colonies in three film-type culture media 60 is smaller than a predetermined value (e.g., "30"). For example, in the case of FIG. 17, the number of colonies in the third film-type culture medium 60 is "140" and the average is "63.3". Therefore, the lot determination processing unit 424 determines that the process is rejected.

The lot determination processing unit 424 of this embodiment may select one of the above-described methods based on the number of the culture medium information registered in each process, or may execute the process determination by combining two or three of the above methods. The predetermined condition is alterable depending on the type of specimen and type of bacterium to be detected. Also, the predetermined condition may be set by the manager or may be supplied as a part of a program.

(Line Determination)

The lot determination processing unit 424 executes the line determination of each work line 80 based on the acceptance/rejection determination, in view of sanitary management, of the plural processes determined at the predetermined timing and registered in correspondence with the corresponding line information. Namely, the lot determination processing unit 424 executes the line determination by a total determination based on each determination result of the plural processes of the same lot determined at the predetermined timing.

Specifically, the lot determination processing unit 424 obtains the determination result of the process determination of the process determined at the same timing or at the timing satisfying a predetermined condition and including the line ID of the work line 80 for which the line determination is to be executed as described above. The lot determination processing unit 424 determines that the line determination of the work line 80 to be determined is acceptable when the number of the acceptance/rejection of the determination results satisfies the predetermined condition, and determines that the line determination of the work line 80 to be determined is rejected when the number does not satisfy the predetermined condition.

For example, in a case where three processes have the line ID of the work line 80 to be determined, if the first process is "acceptable", the second process is "acceptable", the third process is "rejected", and the predetermined condition is that the work line 80 is acceptable if it includes "60%" acceptable processes, the lot determination processing unit 424 determines that the line determination of the work line 80 to be determined is acceptable.

(Lot Determination)

The lot determination processing unit 424 executes the lot determination of each lot based on the acceptance/rejection determination, in view of sanitary management, of the plural work lines 80 determined at the predetermined timing and registered in correspondence with the corresponding lot information. Namely, the lot determination processing unit 424 executes the lot determination by a total determination based on each determination result of plural work lines 80.

Specifically, the lot determination processing unit 424 executes the lot determination of the lot to be determined based on the acceptance/rejection determination, determined the predetermined timing, of the sanitary management information of the work line 80 having the lot ID of the lot for which the lot determination is to be executed.

For example, when the predetermined condition is that the lot determination processing unit 424 determines that the lot is acceptable if the lot is constituted by the accepted work line 80 of "60%", it is assumed that three work lines 80 has the lot ID of the lot to be determined. In this case, if the first work line 80 is "acceptable", the second work line 80 is "acceptable" and the third work line 80 is "rejected", the lot determination processing unit 424 determines that the lot determination of the lot to be determined is acceptable.

If the work time of the lot is long, the lot determination may be executed by dividing the time into predetermined time periods (e.g., 8 hours or 12 hours). In this case, when the lot determination is executed while the work is being interrupted, a dummy result may be used or the determination can be executed during the interruption of the work.

(Others)

The lot determination processing unit 424 can execute determination and data analysis other than those described above by using the culture medium information, the line information, the lot information and the work management DB 404, and can supply the determination result or the data analysis result to the manager terminal device 20 via the report processing unit 425 in such a manner that the manager can browse.

Specifically, the lot determination processing unit 424 executes the predetermined analysis of the culture medium information or the culture medium reconstruction image data in one culture medium ID in time series from the culture start time to the end of culture, in order to confirm reliability of the specimen cultured in each film-type culture medium 60, i.e., in order to confirm whether or not the inspection error is happening.

For example, the lot determination processing unit 424 extracts plural culture medium information having a specific culture medium ID (the same culture medium ID) 66 from the culture start time to a predetermined time, together with the culture medium reconstruction image data, based on the instruction by the manager received via the manager terminal device 20. Then, the lot determination processing unit 424 executes the predetermined analysis of each culture medium information and each image data along a predetermined time series, or aggregates each culture medium information and each image data in time series. Also, the lot determination processing unit 424 makes the report processing unit 425 generate browsing data of the analysis result or the aggregation result in a predetermined format and supply the generated browsing data to the manager terminal device 20 in a manner browsable by the manager.

At this time, in cooperation with the report processing unit 425, the lot determination processing unit 424 may make each culture medium information in a culture medium ID 66 individually browsable for a statutory sanitary management report based on the instruction by the manager terminal device 20.

The lot determination processing unit 424 may have a search function of the culture medium information, the line information, the lot information or the work management information. Specifically, the lot determination processing unit 424 may search the database 400 by using the lot ID (the instruction sheet ID 71a), the work line ID, the process ID 71b, the work ID 71, the culture start time, the work date and time of the lot, the culture medium ID 66 and the type of specimen as a search key, and cooperates with the report processing unit 425 to generate data of the corresponding culture medium information and various information in a manner browsable by the manager.

The report processing unit 425 may supply information related to the culture medium information (the culture medium reconstruction image data, the number of colonies and the culture medium determination result), the process information, the line information or lot specified by the search in a predetermined report format, based on the instruction by the manager received via the manager terminal device 20. Namely, the report processing unit 425 can supply various kinds of information in a case of a statutory inspection report or else as the proof or the report.

[5.6] Report Processing Unit

Next, the report processing unit 425 in the server device 40 of this embodiment will be described.

The report processing unit 425 generates the analysis result (i.e., the determination result of acceptance/rejection) of the data analysis related to the sanitary management in the designated lot, work line 80 or process as report data, based on the instruction by the manager inputted to the manager terminal device 20 and template data having a predetermined report format, and supplies the generated report data to the manager terminal device 20 via the communication control unit 410 in a manner browsable by the manager.

Specifically, the report processing unit 425 extracts necessary information such as the culture medium reconstruction image data, the number of colonies or the culture medium determination result from the culture medium information, the line information and the lot information, and assigns each information to the template data based on the extracted information and the analysis result obtained by the lot determination processing unit 424 to generate the report data. Then, the report processing unit 425 supplies, to the manager terminal device 20, the report data to which processing such as rotation is not applied and for which the identity of the culture medium image is ensured.

As described above, the report processing unit 425 can generate the predetermined report data or browsing data in accordance with various analysis or search, and supplies them to the manager terminal device 20. Namely, the report processing unit 425 can supply the culture medium information, the process information, the line information or information related to the lot obtained by the search in a predetermined report format, and can supply various information in a statutory inspection report or else as its proof or report.

[6] Operation Processing of Sanitary Management System

[6.1] Registration Processing of Culture Medium Information

Figure 18:
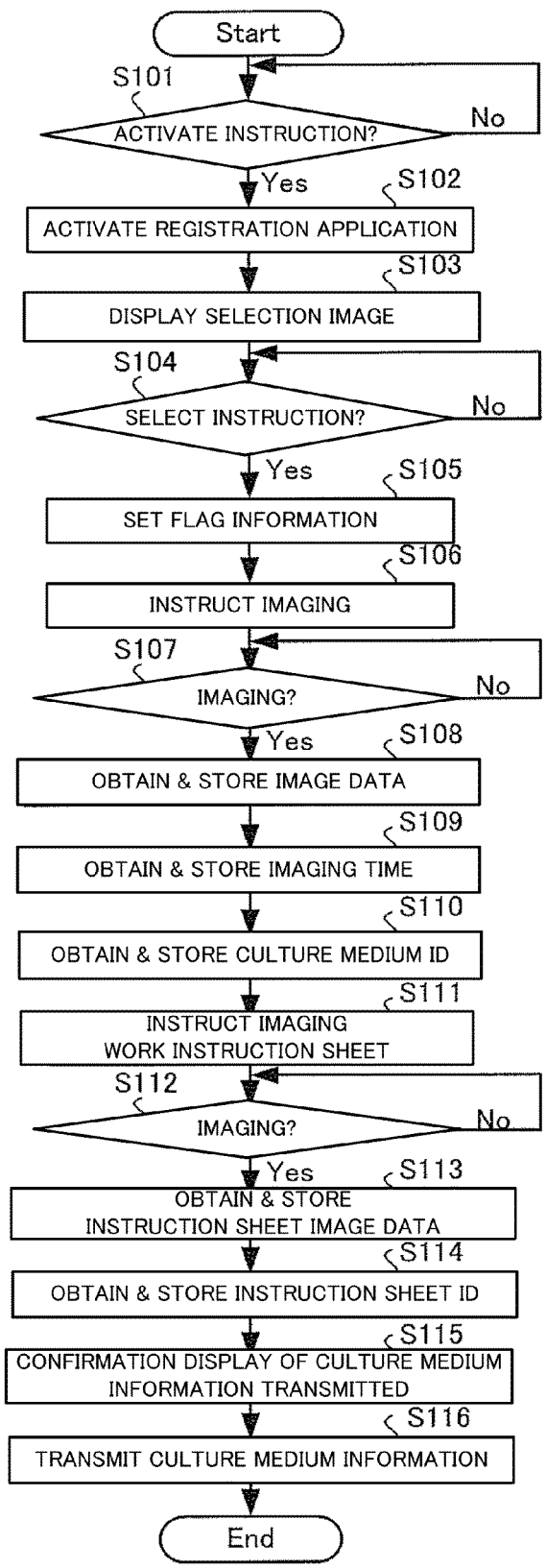
FIG. 18 is a flowchart showing an operation of registration processing of the culture medium information in the portable communication terminal device of the embodiment.
Figure 19B:
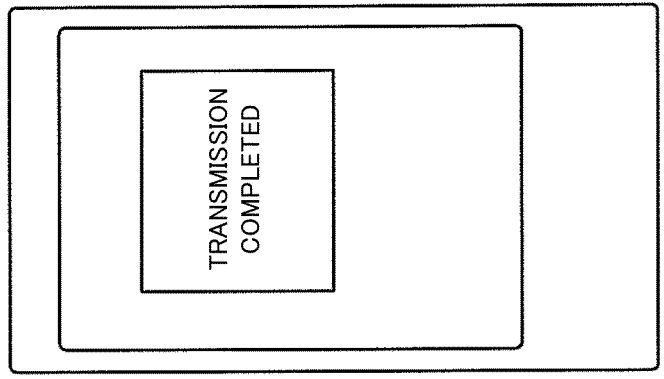
FIGS. 19A and 19B are examples of the image displayed on the display unit when the culture medium information is transmitted by the portable communication terminal device of the embodiment.
Figure 19A:
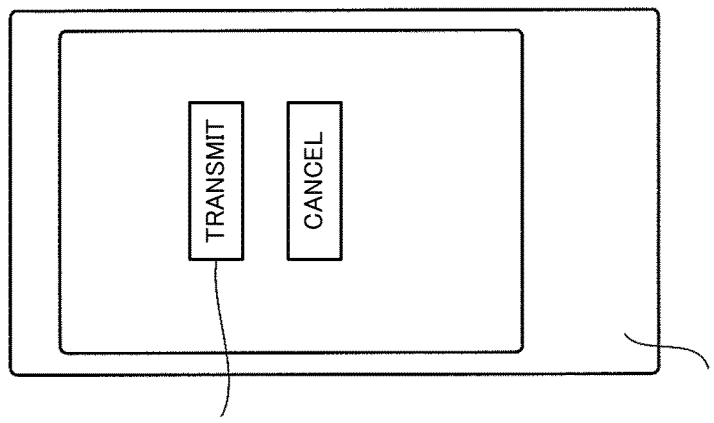
Figure 20:
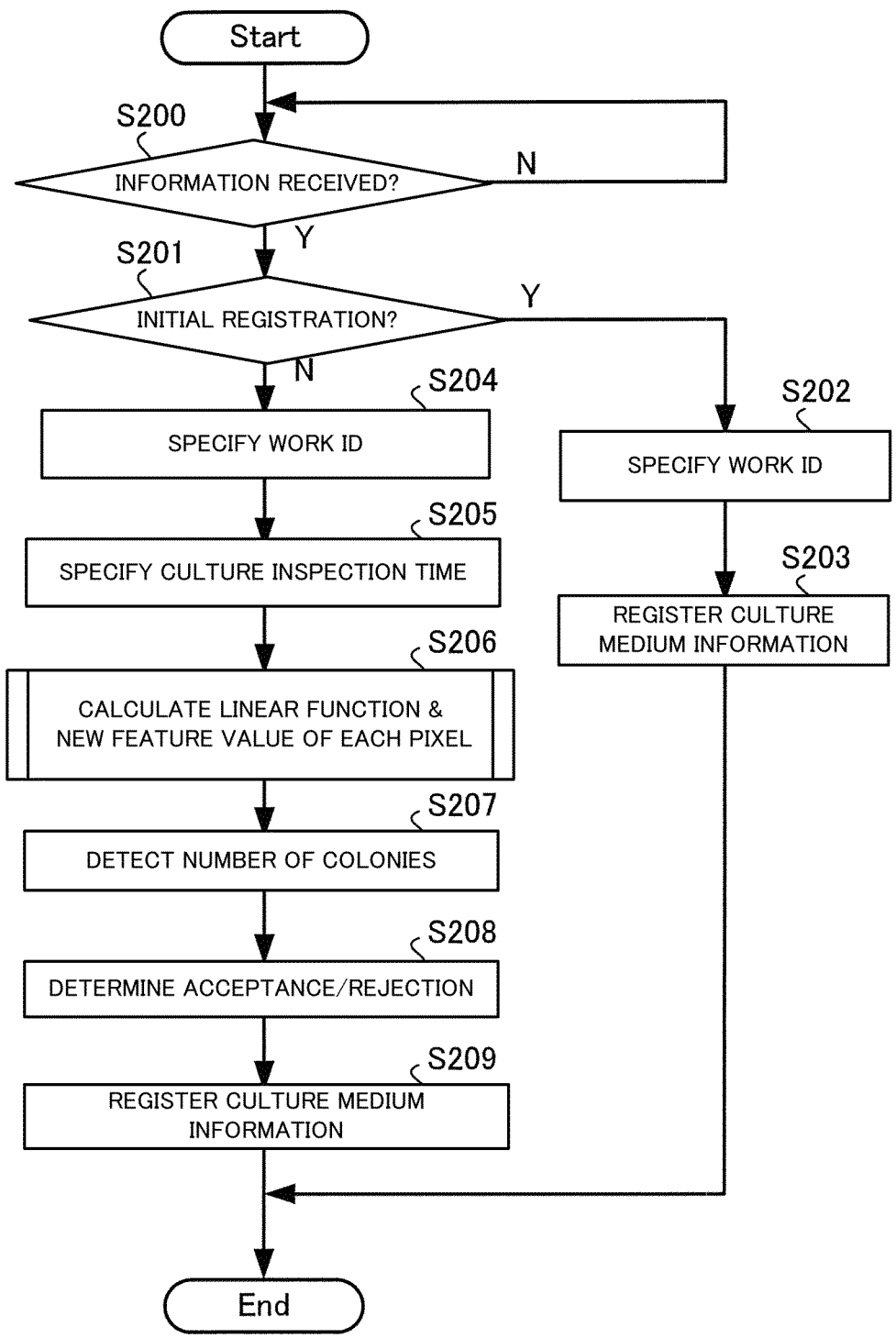
FIG. 20 is a flowchart showing an operation of registration processing of the culture medium information in the server device of the embodiment.

Next, description will be given of registration processing of the culture medium information in the portable communication terminal device 10 and the server device 40 of this embodiment with reference to FIGS. 18 to 20. FIG. 18 is a flowchart showing an operation of the registration processing of the culture medium information in the portable communication terminal device 10 of this embodiment, and FIGS. 19A and 19B are examples of the image displayed on the display unit 160 when the culture medium information is transmitted by the portable communication terminal device 10. FIG. 20 is a flowchart showing an operation of the registration processing of the culture medium information in the server device 40 of this embodiment.

In this operation, it is assumed that the line information DB 402 and the lot information DB 403 already store the lot information and the line information in correspondence with the work instruction sheet 70. It is also assumed that the film-type culture medium 60 and the work instruction sheet 70 are provided with the culture medium ID or the instruction sheet ID in a form of two-dimensional barcode. Further, in this operation, it is assumed that the detection of the number of colonies in each film-type culture medium 60 is executed when the culture medium information is registered with the database 400.

First, in the portable communication terminal 10, when the application control unit 120 detects an activation instruction of the culture medium registration application via the operation unit 170 (step S101), it reads out the culture medium registration application from the application storage unit 101 and activates it (step S102). At this time, the application control unit 120 executes necessary processing such as an initialization of the work memory and else under the control of the portable terminal management control unit 190.

Next, the application control unit 120 cooperates with the display control unit 161 to display the image for selecting one of the initial registration of the film-type culture medium 60 or the post-culture registration after the passage of the predetermined time from the start of culture, on the display unit 160, and waits for the input (step S103). For example, the application control unit 120 cooperates with the display control unit 161 to display the image shown in FIG. 5 on the display unit 160.

Next, when the application control unit 120 detects the input of the selection instruction by the operation unit 170 (step S104), it determines whether it is the initial registration or the post-culture registration and sets the result to the flag information (step S105).

Next, the application control unit 120 displays the image suggesting the imaging of the film-type culture medium 60 on the display unit 160, and cooperates with the operation unit 170 to wait for the imaging by the image data generation unit 110 (step S106). For example, the application control unit 120 cooperates with the display control unit 161 to display the image shown in FIG. 6A on the display unit 160.

Next, the application control unit 120 cooperates with the image data generation unit 110, the display control unit 161 and the operation unit 170 to detect the imaging by the image data generation unit 110 (step S107), obtain the culture medium image data of the film-type culture medium 60 imaged by the image data generation unit 110 together with the culture medium ID 66, and store it in the image data storage unit 102 with the predetermined image ID (step S108).

Next, the application control unit 120 obtains the current time from the timer 180 as the imaging time of the culture medium image data, and stores it in the image data storage unit 102 as the metadata in correspondence with the culture medium image data (step S109).

Next, the application control unit 120 analyses the two-dimensional barcode formed on the predetermined area of the obtained culture medium image data to obtain the culture medium ID 66, and stores it in the image data storage unit 102 in correspondence with the culture medium image data (step S110).

Next, the application control unit 120 cooperates with the display control unit 161 to display the image for obtaining the instruction sheet ID 71a, the process ID 71b and the instruction sheet image data on the display unit 160 and wait to obtain the instruction sheet image data (step S111). For example, the application control unit 120 cooperates with the display control unit 161 to display the image shown in FIG. 7A on the display unit 160.

Next, the application control unit 120 cooperates with the image data generation unit 110, the display control unit 161 and the operation unit 170 to detect the imaging by the image data generation unit 110 (step S112), obtain the instruction sheet image data in which the work ID 71 is imaged, and store it in the image data storage unit 102 in correspondence with the culture medium image data obtained in step S108 (step S113).

When obtaining the process ID 71b as the work ID 71 or obtaining one process ID 71b from plural process IDs 71b, the application control unit 120 cooperates with the display control unit 161 and the operation unit 170 to execute a display to make the user select the process ID 71b to be obtained, and obtain the corresponding process ID 71b.

Next, the application control unit 120 analyses the two-dimensional barcode formed on the predetermined area of the instruction sheet image data and the culture medium image data to obtain the work ID 71, and stores it in the image data storage unit 102 in correspondence with the instruction sheet image data (step S114).

Next, the application control unit 120 obtains the current time from the timer 180 as the imaging time of the culture medium image data, cooperates with the display control unit 161 and the operation unit 170 to make the worker confirm the instruction sheet image data, the work ID 71, the culture medium image data, the culture medium ID 66 and the imaging time thus obtained (step S115).

The application control unit 120 may obtain the culture medium image data again, based on the instruction by the worker, at the time when the worker confirms the obtained culture medium information. Also, at this time, the application control unit 120 may cooperate with the display control unit 161 and the operation unit 170 to permit the worker to correct the culture medium image data.

Next, the application control unit 120 transmits the obtained image data, its metadata and the flag information indicating the initial registration or the post-culture registration as the culture medium information to the server device 40 via the network communication unit 130, together with the terminal ID and the work instruction ID, based on the instruction by the worker (step S116), and then ends the registration processing by the portable communication terminal device 10.

At this time, the display control unit 161 displays the image shown in FIGS. 19A and 19B on the display unit 160. Also, the network communication unit 130 executes login for the access to the server device 40 based on the terminal ID and/or the inputted ID and the password at the time of transmitting the culture medium information, and establishes the communication line with the server device 40 after the completion of the login to transmit the culture medium information.

As the registration processing of the culture medium information based on the transmitted culture medium information, the server device 40 executes the following processing as separate processing.

First, in the server device 40, when the communication control unit 410 receives the culture medium information transmitted from the portable communication terminal device 10 (step S200), the registration processing unit 421 determines whether it is the initial registration or the post-culture registration based on the flag information included in the received culture medium information (step S201). At this time, the process goes to step S202 when it is determined to be the initial registration, and the process goes to the step S204 when it is not determined to be the initial registration, i.e., the post-culture registration.

Next, when the registration processing unit 421 determines the initial registration, it extracts and specifies the work ID 71 included in the culture medium information (step S202).

Next, the registration processing unit 421 registers the culture medium information with the culture medium information DB 401, based on the specified work ID 71 (step S203), and ends the operation. While the culture start time is stored in the work management DB 404 in advance, the registration processing unit 421 may register the imaging time included in the received culture medium information with the work management DB 404 as the culture start time in the process of step S203.

On the other hand, when the register processing unit 421 determines the post-culture registration, it extracts and specifies the work ID 71 included in the culture medium information (step S204), and specifies the culture medium inspection time for registering the culture medium information based on the imaging time included in the culture medium information (step S205).

At this time, the registration processing unit 421 may cooperate with the portable communication terminal device 10 to make the portable communication terminal device 10 designate the culture inspection time for registering the culture medium information and register it, or may register the imaging time included in the received culture medium information as it is as the culture inspection time. Also, the registration processing unit 421 may manage the culture medium registration at the time of the culture inspection time already executed, and specify the culture medium inspection time based on the timing of receiving the culture medium information and the culture inspection time already used for the registration of the culture medium information. Namely, the registration processing unit 421 may rewrite the execution flag every time the registration of the culture medium information is executed, and specify the culture inspection time in comparison with the received imaging time, by referring to the information of the execution flag.

Next, the registration processing unit 421 makes the image analysis processing unit 422 execute the image analysis of the received culture medium image data, and execute the calculation processing of the linear function prescribing the relation of two or more feature values in each pixel and the calculation processing of the new feature value of each pixel based on the linear function (step S206).

The calculation processing of the linear function and the calculation processing of the new feature value of each pixel based on the linear function will be described later. At this time, the image analysis processing unit 422 may generate the culture medium reconstruction image based on the new feature value calculated for each pixel and the position information of each pixel on the culture medium image.

Next, the registration processing unit 421 makes the colony detection determination unit 423 detect the colonies of the imaged specimen based on the new feature value of each pixel constituting the culture medium image, and count the number of the colonies (step S207).

Next, the colony detection determination unit 423 reads out the culture medium determination criterion based on the type of the specimen and the bacterium to be detected which are specified based on the work ID 71, and determines whether or not the detected number of colonies satisfies the predetermined condition (step S208). Namely, the colony detection determination unit 423 determines the acceptance (normal) when the predetermined condition is satisfied, and determines the rejection (abnormal) when the predetermined condition is not satisfied.

Instead of the above automatic registration, the colony detection determination unit 423 may cooperate with the portable communication terminal device 10 to display the detected number of colonies and the acceptance/rejection determination result on the display unit 160 of the portable communication terminal device 10 so that the user can be browse and confirm them.

Next, the registration processing unit 421 registers the culture medium image data (or the culture medium reconstruction image data), the recognized culture medium ID 66, the determined acceptance/rejection, the detected number of colonies and the culture start time information having the imaging time included in the culture medium information as the culture start time with the culture medium information DB 401, in correspondence with the specified work ID 71 (step S209), and ends this operation.

The registration processing unit 421 may make the portable communication terminal device 10 display the line information and information to be registered on the display unit 160 and register the culture medium information based on the user instruction inputted via the portable communication terminal device 10.

Also, in a case where the portable communication terminal device 10 transmits the culture medium image data and the server device 40 analyses each image data to recognize the culture medium ID 66, the registration processing unit 421 analyses the culture medium ID 66 imaged on the predetermined area of the received culture medium image data to obtain the culture medium ID 66 in step S201. Similarly, the work ID 71 on the instruction sheet image data is recognized by the server device 40.

[6.2] Calculation Processing of Linear Function and New Feature Value

Figure 21:
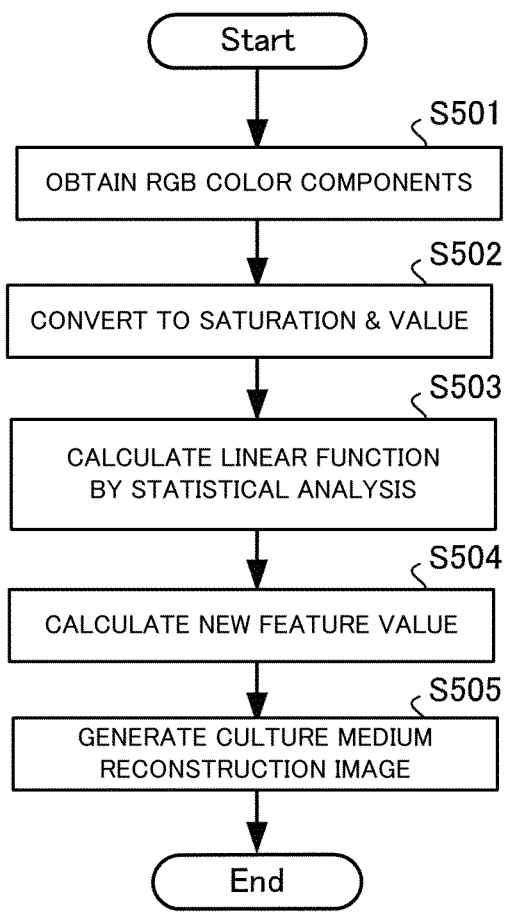
FIG. 21 is a flowchart showing an operation of calculation processing of the linear function and the new feature value in the server device of the embodiment.

Next, the calculation processing of the linear function and the new feature value in the server device 40 of the embodiment will be described with reference to FIG. 21. FIG. 21 is a flowchart showing an operation of the calculation processing of the linear function and the new feature value in the server device 40 of the embodiment.

This operation is executed by the image analysis processing unit 422, under the control of the registration processing unit 421, in step S206 of the culture medium registration processing shown in FIG. 20. In this operation, the saturation and value are extracted from the plural RGB color components, and the conversion processing of the new feature value is executed based on the saturation and value. In this operation, the culture medium reconstruction image is generated based on the new feature value of the pixels constituting the culture medium image and the position information in the culture medium image.

First, the image analysis processing unit 422 obtains plural color components of R (Red), G (Green) and B (Blue) of each pixel constituting the culture medium image obtained from the culture medium image data (step S501), and converts each value in the color space (RGB color space) thus obtained to the values of the saturation and the value in the HSV color space (step S502).

Next, the image analysis processing unit 422 executes the statistical analysis based on the distribution of the pixels of the culture medium image by using the coordinate system prescribed by the saturation and value of each pixel, and calculates the linear function prescribing the relation of two or more feature values in each pixel (step S503).

For example, the image analysis processing unit 422 executes the regression analysis or the principal component analysis as the statistical analysis using the two-dimensional coordinate system prescribed by each feature value of the saturation and value, and calculates the regression line or the axis of the first principal component as the linear function.

Next, the image analysis processing unit 422 calculates the new feature value based on the coordinate values of the saturation and value of each pixel constituting the culture medium image and the calculated linear function (step S504). For example, the image analysis processing unit 422 rotates the coordinate values of each pixel by the rotation matrix by using the calculated linear function as a reference axis to calculate the new feature value.

Finally, the image analysis processing unit 422 generates the culture medium reconstruction image based on the calculated new feature value of each pixel and the position information of each pixel on the culture medium image (step S505), and ends the operation.

[6.3] Lot Determination Processing

Figure 22:
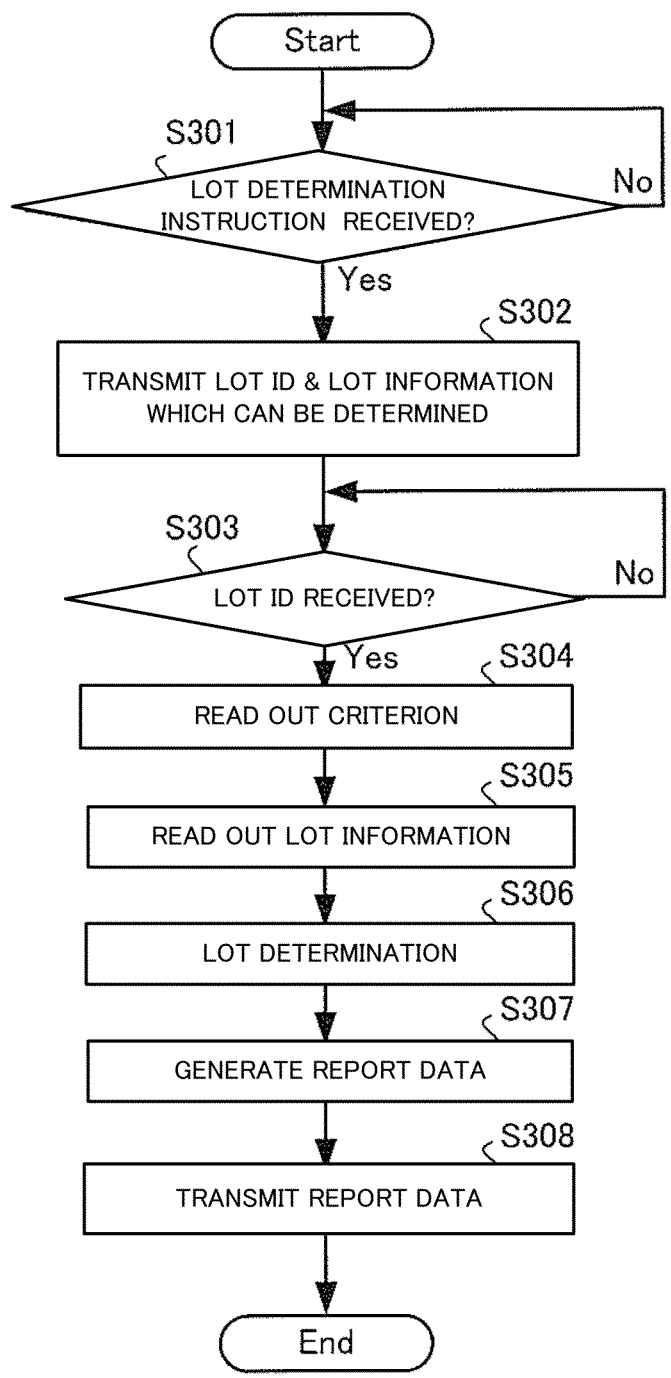
FIG. 22 is a flowchart showing an operation of lot determination processing in the server device of the embodiment.

Next, the operation of the lot determination processing in the server device 40 of this embodiment will be described with reference to FIG. 22. FIG. 22 is a flowchart showing the operation of the lot determination processing in the server device 40 of this embodiment.

In this operation, it is assumed that the corresponding culture medium information has been registered and the process determination criterion information, the line determination criterion information and the lot determination criterion information have been registered in advance.

First, when the communication control unit 410 in the server device 40 receives the instruction of the lot determination transmitted from the manager terminal device 20 (step S301), the lot determination processing unit 424 cooperates with the communication control unit 410 to search the lot ID for which the lot determination is possible, transmits the lot ID of the lot for which the lot determination is possible and the corresponding lot information to the manager terminal device 20 such that the manager can browse and select, and then wait for the instruction of the lot ID for which the lot determination process is executed (step S302).

The manager terminal device 20 displays the lot ID of the lot for which the lot determination is possible on a predetermined display screen in a manner browsable and selectable by the manager.

Next, when the communication control unit 410 receives the lot ID specified by the manager via the manager terminal device 20 (step S303), the lot determination processing unit 424 reads out each of the criterion information indicating the condition of the process determination of the process, the line determination and the lot determination belonging to the lot, from the ROM/RAM 440 (step S304).

Next, the lot determination processing unit 424 reads out the various lot information, the line information and the culture medium information of the corresponding lot ID (step S305), and executes the lot determination with executing the process determination and the line determination, based on the lot information, the line information and the culture medium information thus read out (step S306). Specifically, the lot determination processing unit 424 executes the process determination of each process specified by the lot information, and executes the line determination of each work line 80 specified by the lot information based on the process determination result of the process determination. Then, the lot determination processing unit 424 executes the lot determination based on the line determination result.

Next, the lot determination processing unit 424 reads out the predetermined template serving as the report form of the determination, and assigns the lot determination result to the template to generate the report data (step S307).

Finally, the lot determination processing unit 424 cooperates with the communication control unit 410 to supply the generated report data to the manager terminal device 20 (step S308), and ends this operation.

When receiving the report data, the manager terminal device 20 displays it in a manner browsable by the manager. However, the lot determination processing unit 424 may transmit, not the report data, but print data printable by a printer to the manager terminal device 20.

[7] Modified Examples

[7.1] 1st Modified Example

While the culture medium registration processing and the colony detection determination processing are executed at the same timing, the colony detection determination processing may be executed at any timing.

[7.2] 2nd Modified Example

In this embodiment, instead of executing the registration processing of the culture medium information by using the portable communication terminal device 10 such as the tablet-type information terminal device, the smartphone or the portable telephone, the registration processing of the culture medium information may be realized by using a personal computer of laptop type or desktop type, and an image input device such as a scanner, a digital camera or a smartphone.

In this case, the personal computer and the image input device may be connected by a predetermined communication standard to integrally use the personal computer and the image input device to realize the registration processing of the culture medium information. Alternatively, the culture medium image data and the instruction sheet image data obtained in advance may be stored in a physical memory such as a memory card and the like, and each image data thus stored may be read out by the personal computer to realize the registration processing of the culture medium information.

[7.3] 3rd Modified Example

In this embodiment, the portable communication terminal device 10, the manager terminal device 20 and the server device 40 may be placed and used in the same site, or may be separately placed at remote locations such as places outside the country, or may be used at the remote locations to execute each processing described above. However, it is the premise that the portable communication terminal device 10 is used in the same lot.

[7.4] 4th Modified Example

In this embodiment, the culture medium information in the specimen cultured in the film-type culture medium 60 is registered. However, the culture medium information of the specimen cultured in an agar medium may be registered.

[7.5] 5th Modified Example

In this embodiment, instead of obtaining the culture medium ID 66 by imaging the film-type culture medium ID 60 by the image data generation unit 110, the worker may input the culture medium ID 66.

In this case, the application control unit 120 cooperates with the display control unit 161 and the operation unit 170 to make the worker directly and manually input the culture medium ID 66 via the operation unit 170.

The application control unit 120 controls the display control unit 161 and the operation unit 170 to enable the selection of the displayed items in a pull-down menu by a click or touch selection, and makes the worker input the culture medium ID 66.

[7.6] 6th Modified Example

In this embodiment, various processing is executed by a single server device 40. However, various processing may be executed by a server system including plural server devices.

As described above, in the sanitary management system S of the embodiment, it is possible to eliminate feature values other than the feature values extracted from each pixel constituting the culture medium image and to detect the colony by focusing on the contrast of the image with respect to the extracted feature values. Therefore, it is possible to improve the accuracy in detecting the number of colonies and to precisely detect the colonies with preventing erroneous detection.

Particularly, in the sanitary management system S of the embodiment, since the feature values of each pixel can be converted to a new feature value based on the calculated linear function and the contrast can be enhanced between the color of the culture medium and the color of the colony, it is possible to easily and precisely classify the pixels into the colony pixels and the culture medium pixels by using binarization processing or Hough transform, for example.

Also, in the sanitary management system S of the embodiment, since the linear function can be calculated along the scattering direction of each pixel constituting the culture medium image, it is possible to precisely calculate the linear function prescribing the contrast based on the extracted feature values.

Also, in the sanitary management system S of the embodiment, since the linear function can be calculated based on the versatile statistical analysis such as the regression analysis or the principal component analysis, it is possible to easily execute arithmetic processing with a simple configuration.

Further, in the sanitary management system S of the embodiment, since the linear function can be calculated by using not only each RGB color components simply extracted from the pixel but also various color components such as hue and value, it is possible to calculate an appropriate linear function.

Then, in the sanitary management system S of the embodiment, resources can be saved in comparison with the case of executing and providing various data analysis by using physical resources such as a paper medium, and registration error can be remarkably reduced by registering the culture medium information related to the culture medium with the database. Therefore, difficult management of the culture medium can performed easily, and resources can be saved without wastefully consuming the culture media.

INDUSTRIAL APPLICABILITY

This invention can be used for a sanitary management system for food.

DESCRIPTION OF REFERENCE NUMERALS

S Sanitary management system
10 Portable communication terminal device
20 Manager terminal device
30 Network
40 Server device
60 Film-type culture medium
70 Work instruction sheet
80 Work line
100 Data storage unit
101 Application storage unit
102 Image data storage unit
110 Image data generation unit
120 Application control unit
130 Network communication unit
140 Short-range wireless communication interface
150 Current position detection unit
160 Display unit
170 Operation unit
180 Timer
190 Portable terminal management control unit
400 Database
401 Culture medium information DB
402 Line information DB
403 Lot information DB
404 Work management DB
410 Communication control unit
420 Data processing unit
421 Registration processing unit
422 Image analysis processing unit
423 Colony detection determination unit
424 Lot determination processing unit
425 Report processing unit
430 Server management control unit

The invention claimed is:

1. A culture medium information registration system comprising:
    an obtaining unit which obtains culture medium image data including a culture medium image created by imaging a culture medium on which food is cultured as a specimen;
    an extracting unit which extracts two or more feature values related to a color of each pixel constituting the culture medium image;
    a calculation unit which executes statistical analysis based on distribution of pixels of the culture medium image by using a coordinate system prescribed by the extracted two or more feature values of each pixel, and calculates a model function prescribing relation of the two or more feature values in each pixel;
    a detection unit which detects colonies in the culture medium image based on the calculated model function;
    a count unit which counts a number of detected colonies; and
    a registration unit which registers information related to the culture medium including at least the counted number of colonies with a database as culture medium information.

2. The culture medium information registration system according to claim 1, wherein the calculation unit calculates an axis parallel with a scattering direction of pixels on the coordinate system as the model function, based on coordinate values on the coordinate system of each pixel prescribed by the two or more feature values, as the statistical analysis.

3. The culture medium information registration system according to claim 2, wherein the calculation unit executes regression analysis based on the two or more feature values of each pixel and calculates a regression line as the model function, as the statistical analysis.

4. The culture medium information registration system according to claim 2, wherein the calculation unit executes principal component analysis based on the two or more feature values of each pixel and calculates an axis of a first principal component as the model function, as the statistical analysis.

5. The culture medium information registration system according to claim 1, wherein the extracting unit extracts at least two or more color components from the color components of each pixel as the feature values.

6. The culture medium information registration system according to claim 1, wherein the extracting unit obtains plural color components of each pixel, and extracts a feature value obtained by converting a color space of the obtained color components as the feature values.

7. The culture medium information registration system according to claim 1, further comprising a converting unit which converts coordinate values of each pixel in a coordinate space prescribed by the extracted two or more feature values to a new feature value based on the calculated model function,
wherein the detection unit detects the colonies in the culture medium image based on the new feature value.

8. The culture medium information registration system according to claim 7, wherein the detection unit classifies the pixel of the culture medium image to culture medium pixels constituting the culture medium and colony pixels constituting colonies cultured on the culture medium, based on the new feature value and a given threshold value, to detect the colonies.

9. The culture medium information registration system according to claim 7, further comprising an image generation unit which generates a reconstruction image based on the new feature value of each pixel and position information of each pixel on the culture medium image,
wherein the registration unit registers the generated reconstruction image with the database as the culture medium information.

10. A program stored in a non-transitory tangible computer-readable medium and executed by a computer, making the computer function as:
an obtaining unit which obtains culture medium image data including a culture medium image created by imaging a culture medium on which food is cultured as a specimen;
an extracting unit which extracts two or more feature values related to a color of each pixel constituting the culture medium image;
a calculation unit which executes statistical analysis based on distribution of pixels of the culture medium image by using a coordinate system prescribed by the extracted two or more feature values of each pixel, and calculates a model function prescribing relation of the two or more feature values in each pixel;
a detection unit which detects colonies in the culture medium image based on the calculated model function;
a count unit which counts a number of detected colonies; and
a registration unit which registers information related to the culture medium including at least the counted number of colonies with a database as culture medium information.

11. A colony detection device comprising:
an obtaining unit which obtains culture medium image data including a culture medium image created by imaging a culture medium on which food is cultured as a specimen;
an extracting unit which extracts two or more feature values related to a color of each pixel constituting the culture medium image;
a calculation unit which executes statistical analysis based on distribution of pixels of the culture medium image by using a coordinate system prescribed by the extracted two or more feature values of each pixel, and calculates a model function prescribing relation of the two or more feature values in each pixel;
a detection unit which detects colonies in the culture medium image based on the calculated model function; and
a count unit which counts a number of detected colonies.

12. A program stored in a non-transitory tangible computer-readable medium and executed by a computer, making the computer function as:
an obtaining unit which obtains culture medium image data including a culture medium image created by imaging a culture medium on which food is cultured as a specimen;
an extracting unit which extracts two or more feature values related to a color of each pixel constituting the culture medium image;
a calculation unit which executes statistical analysis based on distribution of pixels of the culture medium image by using a coordinate system prescribed by the extracted two or more feature values of each pixel, and calculates a model function prescribing relation of the two or more feature values in each pixel;
a detection unit which detects colonies in the culture medium image based on the calculated model function; and
a count unit which counts a number of detected colonies.

13. A sanitary management system comprising:
a communication terminal device which generates a culture medium image by imaging a culture medium on which food is cultured as a specimen, as culture medium image data; and
a server device which detects colonies generated on the culture medium based on the culture medium image data to register with a database,
wherein the server device comprises:
an obtaining unit which obtains the culture medium image data from the communication terminal device;
an extracting unit which extracts two or more feature values related to a color of each pixel constituting the culture medium image;
a calculation unit which executes statistical analysis based on distribution of pixels of the culture medium image by using a coordinate system prescribed by the extracted two or more feature values of each pixel, and calculates a model function prescribing relation of the two or more feature values in each pixel;
a detection unit which detects colonies in the culture medium image based on the calculated model function;
a count unit which counts a number of detected colonies; and
a registration unit which registers information related to the culture medium including at least the counted number of colonies with a database as culture medium information.

* * * * *